(12) United States Patent
Corder et al.

(10) Patent No.: US 7,423,141 B2
(45) Date of Patent: Sep. 9, 2008

(54) INHIBITORS OF ENDOTHELIN-1 SYNTHESIS

(75) Inventors: Roger Corder, Harrow (GB); Adrian P. L. Smith, London (GB); Timothy W. Higgenbottam, Sheffield (GB); Martine Rothblatt, Silver Spring, MD (US); John Vane, London (GB); Delphine Dominique Marthe Lees, London (GB)

(73) Assignee: William Harvey Research Ltd., London (GB)

(*) Notice: Subject to any disclaimer, the term of this patent is extended or adjusted under 35 U.S.C. 154(b) by 511 days.

(21) Appl. No.: 10/295,942

(22) Filed: Nov. 18, 2002

(65) Prior Publication Data

US 2003/0109480 A1    Jun. 12, 2003

Related U.S. Application Data

(63) Continuation of application No. 09/527,240, filed on Mar. 17, 2000, now abandoned.

(60) Provisional application No. 60/125,000, filed on Mar. 18, 1999.

(51) Int. Cl.
*C07H 21/04* (2006.01)
(52) U.S. Cl. .................................................. 536/24.5
(58) Field of Classification Search ........................ None
See application file for complete search history.

(56) References Cited

U.S. PATENT DOCUMENTS

| | | | | |
|---|---|---|---|---|
| 4,306,075 | A | * | 12/1981 | Aristoff .......................... 560/56 |
| 5,034,506 | A | | 7/1991 | Summerton et al. |
| 5,602,204 | A | | 2/1997 | Harimoto et al. |
| 5,688,499 | A | * | 11/1997 | Banting et al. ............. 424/78.35 |
| 5,747,340 | A | * | 5/1998 | Harats et al. .................. 435/456 |
| 5,994,076 | A | * | 11/1999 | Chenchik et al. ................ 435/6 |
| 6,054,486 | A | * | 4/2000 | Crow et al. ................... 514/571 |
| 6,551,795 | B1 | * | 4/2003 | Rubenfield et al. ........... 435/69.1 |

FOREIGN PATENT DOCUMENTS

| | | | |
|---|---|---|---|
| EP | 0 347 243 A | | 12/1989 |
| WO | WO 92/20823 | | 11/1992 |
| WO | WO 9608268 A1 | * | 3/1996 |
| WO | WO 99/11778 | | 3/1999 |

OTHER PUBLICATIONS

D'Orleans-Juste et al. (1997) Mol. Cell. Biochemistry 172:199-211.*
Kurreck (2003) Eur. J. Biochem. 270:1628-1644.*
Lin et al. (2002) J. Cardiovascular Pharmacology 39:590-599.*
Gerwirtz et al. (1998) Blood 92(3):712-736.*
Jen et al. (2000) Stem Cells 18:307-319.*
Opalinska et al. (2002) Nature Reviews 1:503-514.*
Schriffin et al. (1997) J. Hypertension 15:57-63.*
Weir (1998) AJH 11:163S-169S.*
K.M. McCulloch et al., British Journal of Pharmacology, "Endothelin receptors mediating contraction of rat and human pulmonary resistance arteries: effect of chronic hypoxia in the rat," vol. 123, pp. 1621-1630 (1998).
B.M. Löffler et al., Federation of European Biochemical Societies, "Effect of different endothelin receptor antagonists and of the novel non-peptide antagonist Ro 46-2005 on endothelin levels in rat plasma," vol. 333, No. 1,2, pp. 108-110 (1993).
T. Fukuroda et al., Biochemical and Biophysical Research Communications, "Clearance of Circulating Endothelin-1 by ETB Receptors in Rats," vol. 199, No. 3, pp. 1461-1465 (1994).
P.J. Barnes, Br. J. Clin. Pharmacol, "Pathophysiology of asthma," vol. 42, pp. 3-10 (1996).
P.J. Barnes, Brief Review, "Endothelins and pulmonary diseases," pp. 1051-1059 (1994).
M.J. Carr et al., European Respiratory Journal, "Distribution of immunoreactive endothelin in the lungs of mice during respiratory viral infection," vol. 11, pp. 79-85 (1998).
K.R. Chapman et al., The American Journal of Medicine, "Therapeutic Approaches to Chronic Obstructive Pulmonary Disease: An Emerging Consensus," vol. 100, Suppl. 1A, pp. 1A-5S-1A-10S (1996).
S.J. Chen et al., Journal of Cardiovascular Pharmacology, "The Orally Active Nonpeptide Endothelin A-Receptor Antagonist A-127722 Prevents and Reverses Hypoxia-Induced Pulmonary Hypertension and Pulmonary Vascular Remodeling in Sprague-Dawley Rats," vol. 29, pp. 713-725 (1997).
R. Corder et al., Journal of Cardiovascular Pharmacology, "Cytokine Regulation of Endothelin-1 Release from Bovin Aortic Endothelial Cells," vol. 26, Suppl. 3, pp. S56-S58 (1995).
V.S. diCarlo et al., "$ET_A$-receptor antagonist prevents and reverses chronic hypoxia-induced pulmonary hypertension in rat," pp. L690-L697 (1995).
A. Giaid et al., The New England Journal of Medicine, "Reduced Expression of Endothelial Nitric Oxide Synthase in the Lungs of Patients with Pulmonary Hypertension," vol. 333, No. 4, pp. 214-221 (1995).
D. W.P. Hay et al., The Journal of Pharmacology and Experimental Therapeutics, vol. 284, No. 2, "Functional and Binding Characterization of Endothelin Receptors in Human Bronchus: Evidence for a Novel Endothelin B Receptor Subtype?," pp. 669-677 (1998).
W.G. Haynes et al., Journal of Hypertension, vol. 16, No. 8, "Endothelin-1 as a regulator of cardiovascular function in health anthesease," pp. 1081-1098 (1998).
M. Hoshino et al., Thorax, vol. 53, "Expression of growth factors and remodelling of the airway wall in bronchial asthma," pp. 21-27 (1998).
P.K. Jeffery, Thorax, vol. 53, "Structural and inflammatory changes in COPD: a comparison with asthma," pp. 129-136 (1998).
A. Jeppsson et al., Transplantation, vol. 66, No. 6, "Distribution of Endothelin-I in Transplanted Human Lungs," pp. 806-809 (1998).

(Continued)

*Primary Examiner*—Sean McGarry
*Assistant Examiner*—Louis Wollenberger
(74) *Attorney, Agent, or Firm*—Evelyn H. McConathy; Montgomery, McCracken, Walker & Rhoads, LLP

(57) ABSTRACT

Sequences in human preproendothelin-1 mRNA are described against which antisense oligonucleotides can be used to inhibit the synthesis of endothelin-1. This inhibition of endothelin-1 synthesis may be used to treat diseases where excess production of endothelin-1 is an underlying cause of the symptoms.

6 Claims, 19 Drawing Sheets

OTHER PUBLICATIONS

P. Klemm et al., Proc. Natl. Acad. Sci. USA, vol. 92, "Endothelin 1 mediates ex vivo coronary vasoconstriction caused by exogenous and endogenous cytokines," pp. 2691-2695 (1995).

K. Malarkey et al., British Journal of Pharmacology, vol. 116, "Stimulation by endothelin-1 of mitogen-activated protein kinases and DNA synthesis in bovine tracheal smooth muscle cells," pp. 2267-2273 (1995).

M. Marini et al., Biochemical and Biophysical Research Communications, vol. 220, "Endothelin-1 Induces Increased Fibronectin Expression in Human Bronchial Epithelial Cells," pp. 896-899 (1996).

B.E. Marshall et al., The Lung: Scientific Foundations, Chapter 5.2.6, "Pulmonary Hypertension," pp. 1177-1187 (1991).

C.D. McDermott et al., Journal of Cardiovascular Pharmacology, vol. 31, Suppl. 1, "Immunohistochemical Localization of Endothelin-1 and Endothelin-Converting Enzyme-1 in Rat Lung Allografts," pp. S27-S30 (1998).

J.W. Nyce et al., Nature, vol. 385, "DNA antisense therapy for asthma in an animal model," pp. 721-725 (1997).

M. Nootens et al., JACC, vol. 26, No. 7, "Neurohormonal Activation in Patients With Right Ventricular Failure From Pulmonary Hypertension: Relation to Hemodynamic Variables and Endothelin Levels," pp. 1581-1585 (1995).

R.A. Panettieri, Jr. et al., British Journal of Pharmacology, vol. 118, "Endothelin-1 induced potentiation of human airway smooth muscle proliferation: an $ET_A$ receptor-mediated phenomenon," pp. 191-197 (1996).

D.J. Riley, The Lung: Scientific Foundations, Chapter 5.2.7, "Vascular Remodeling," pp. 1189-1198 (1991).

A.E. Redington et al., J. Allergy Clin. Immunol., vol. 100, No. 4, "Immunoreactive endothelin in bronchial biopsy specimens: Increased expression in asthma and modulation by corticosteroid therapy," pp. 544-552 (1997).

C.R. Roberts, "Is Asthma a Fibrotic Disease?," Chest, vol. 107, No. 3, Session 4, 37th Annual Aspen Lung Conference, pp. 111S-117S (1995).

G. Sun et al., Peptides, vol. 18, No. 9, "Endothelin-1 Induces Bronchial Myofibroblast Differentiation," pp. 1449-1451 (1997).

S. Takeda et al., Ann Thorac Surg., vol. 63, "Experimental Bronchiolitis Obliterans Induced by In Vivo HVI-Liposome-Mediated Endothelin-1 Gene Transfer," pp. 1562-1567 (1997).

D.C. Underwood et al., Journal of Cardiovascular Pharmacology, "Chronic Hypoxia-Induced Cardiopulmonary Changes in Three Rat Strains: Inhibition by the Endothelin Receptor Antagonist," vol. 31, Suppl. 1, pp. S453-S455 (1998).

D.C. Underwood et al., The Journal of Pharmacology and Experimental Therapeutics, vol. 283, No. 3, "Nonpeptide Endothelin Receptor Antagonists. X. Inhibition of Endothelin-1- and Hypoxia-Induced Pulmonary Pressor Responses in the Guinea Pig by the Endothelin Receptor Antagonist, SB 217242," pp. 1130-1137 (1997).

B.R. Wiggs et al., "On the mechanism of mucosal folding in normal and asthmatic airways," pp. 1814-1821 (1997).

J.F. Milligan et al., Journal of Medicinal Chemistry, vol. 36, No. 14, "Current concepts in Antisense Drug Design," pp. 1923, 1993).

Y. Itoh et al., Federation of European Biochemical societies, vol. 231, No. 2, "Cloning and sequence analysis of cDNA encoding the precursor of a human endothelium-derived vasoconstrictor peptide, endothelin: identity of human and porcine endothelin," pp. 440-444 (1988).

Corder et al., Biochemical and Biophysical Research Communications, vol. 207, No. 1, "A simple method for isolating human endothelin converting enzyme free from contamination by neutral endopeptidase 24.11," pp. 355-362 (1995).

C-J. S. Edgell et al., Proc., Natl. Acad. Sci. USA, vol. 80, "Permanent cell line expressing human factor VIII-related antigen established by hybridization," pp. 3734-3737 (1983).

P.E. Nielsen et al., Science, vol. 254, "Sequence-Selective Recognition of DNA by Strand Displacement with a Thymine-Substituted Polyamide," pp. 1497-1500 (1991).

E. Uhlmann et al., Chemical Reviews, vol. 90, No. 4, "Antisense Oligonucleotides: A New Therapeutic Principle," pp. 544-584 (1990).

Onoda et al., J. Neurosurg, vol. 85, "Inhibition of vascular contraction by intracisternal administration of preproendothelin-1 mRNA antisense oligoDNA in a rat experimental vasospasm model," pp. 846-852 (1996) XP-000946190.

Andrea D. Branch, A good antisense molecule is hard to find, TIBS 23—Feb. 1998, pp. 45-50.

Kuang-Yu Jen et al., Suppression of Gene Expression by Targeted Disruption of Messenger RNA; Available Options and Current Strategies, Stem Cells, 2000; 18: pp. 307-319.

* cited by examiner

```
  1 cugcgccaggcgaacggguccugcgccucuccugcaguccagcucuccaccgcccgcgugcgccugcagacgcucccgcgcucgcugccuu
                                                 WH10-cgagggtggcggcgcac WH11-ctgcgaggcgagcgacgag
                                                 WH10A-cgagggtggcggcgcac WH11A-ctgcgaggcgagcgacgg
                                                  WH10B-agaggtggcggcgcac WH11B-gcgaggcgagcgacggaa
                                                   WH10C-cgagggtgcgggcgc  WH11C-ctgcgaggcgacgac
                                                    WH10D-agtggcggcgcacgc    WH11D-gaggcgagcgacggaa
                                                     WH10E-agaggtggcggcgcac      WH11E-gcgaggcgagcgacgg WH20-gacgcggtccgcttgcccag
        WH21-gcttgccagacgcggagg
            WH22-gacgcggaggacgtcaggt
               WH23-ggaggacgtcaggtcgaga
                      WH24-gtggcggcgcacgcggacgt
                                  WH25-ggacgtctgcgaggcgagcg 87 cucucucuggcaggcgcugcuuuucucccguuaaagggcacuuggcugaaggaucgcuuugagaucugaaggaccgcagcgcuuugagggaccugaagcug
                                S1-caatttcccgtgaacccgac
                                S1A-caatttcccgtgaacccg
                                S1B-atttcccgtgaacccgac
                                S1C-caatttcccgtgaacc
                                S1D-ttcccgtgaacccgac
                                S1E-atttcccgtgaacccg
                                S8-gcaatttcccgtgaaccga
                                     S2-ccgacttcctagcgaaactc
                WH26-gagaggaccgtccgcgacgg
                                     WH27-gggcaatttcccgtgaaccc
                                                       WH28-gaaactctagactcccttggg
                                                                     WH29-tgggcgtcgcgaaactccct
                                                                            WH30-gaaactccctgacttcgac 191 uuuuucuucguuuuccuuuggguucaguuugaacgggaguuuuugauccccuuuuuuucagaauugauuauuugcucaug
     WH31-cccaagtcaaacttgccctc
                                                    WH32-gtcttacctaataaacgagt
                                                      WH33-cttacctaataaacgagtac

MDYLLMIFSLLFVACQGAPETAVLGAELSAVGENGGEKPTPSPPWRLRRSKRCSCSSLM
DKECVYFCHLDIIWVNTPEHVVPYGLGSPRSKRALENLLPTKATDRENRCQCASQKDK
KCWNFCQAGKELRAEDIMEKDWNNHKKGKDCSKLGKKCIYQQLVRGRKIRRSSEEHL
RQTRSETMRNSVKSSFHDPKLKGKPSRERYVTHNRAHW (b)

```
   1 ctgcgccagg cgaacgggtc ctgcgcctcc tgcagtccca gctctccacc gccgcgtgcg
  61 cctgcagacg ctccgctcgc tgccttctct cctggcaggc gctgccttt ctccccgtta
 121 aagggcactt gggctgaagg atcgctttga gatctgagga acccgcagcg ctttgaggga
 181 cctgaagctg tttttcttcg ttttcctttg ggttcagttt gaacgggagg tttttgatcc
 241 ctttttttca gaatggatta tttgctcatg atttctctc tgctgtttgt ggcttgccaa
 301 ggagctccag aaacagcagt cttaggcgct gagctcagcg cggtgggtga acggcggg
 361 gagaaaccca ctcccagtcc accctggcgg ctccgccggt ccaagcgctg ctcctgctcg
 421 tccctgatgg ataaagagtg tgtctacttc tgccacctgg acatcatttg ggtcaacact
 481 cccgagcacg ttgttccgta tggacttgga agccctaggt ccaagagagc cttggagaat
 541 ttacttccca caaggcaac agaccgtgag aatagatgcc aatgtgctag ccaaaaagac
 601 aagaagtgct ggaatttttg ccaagcagga aagaactca gggctgaaga cattatggag
 661 aaagactgga ataatcataa gaaggaaaa gactgttcca agcttgggaa aaagtgtatt
 721 tatcagcagt tagtgagagg aagaaaaatc agaagaagtt cagaggaaca cctaagacaa
 781 accaggtcgg agaccatgag aaacagcgtc aaatcatctt tcatgatcc aagctgaaa
 841 ggcaagccct ccagagagcg ttatgtgacc acaaccgag cacattggtg acagacttcg
 901 gggcctgtct gaagccatag cctccacgga gagccctgtg ccgactctg cactctccac
 961 cctggctggg atcagagcag gagcatcctc tgctggttcc tgactggcaa aggaccagcg
1021 tcctcgttca aaacattcca agaaaggtta aggagttccc caaccatct tcactggctt
1081 ccatcagtgg taactgcttt ggtctcttct ttcatctggg gatgacaatg gacctctcag
1141 cagaaacaca cagtcacatt cgaattc
```

FIG. 18

S1 = 5' CAG CCC AAG TGC CCT TTA AC 3' (antisense to bases 117 to 136)
S2 = 5' CTC AAA GCG ATC CTT CAG CC 3' (antisense to bases 132 to 151)
S3 = 5' AGC TCA GCG CCT AAG ACT GC 3' (antisense to bases 316 to 335)
S4 = 5' TGG CAG AAG TAG ACA CAC TC 3' (antisense to bases 436 to 455)
S5 = 5' CCA AAT GAT GTC CAG GTG GC 3' (antisense to bases 452 to 471)
S6 = 5' TGG TCT CCG ACC TGG TTT GT 3' (antisense to bases 777 to 796)
S7 = 5' ATG TGC TCG GTT GTG GGT CA 3' (antisense to bases 866 to 885)
S8 = 5' AGC CCA AGT GCC CTT TAA CG 3' (antisense to bases 116 to 135)

WH1 = 5' TGA TGT CCA GGT GGC AGA AGTA 3' (antisense to bases 445 to 466)
WH2 = 5' CAA GTC CAT ACG GAA CAA CGTG 3' (antisense to bases 487 to 508)
WH3 = 5' CAT CTA TTC TCA CGG TCT GTTG 3' (antisense to bases 557 to 578)
WH4 = 5' TCT CAT GGT CTC CGA CCT GGTT 3' (antisense to bases 780 to 801)
WH5 = 5' GGT CAC ATA ACG CTC TCT GGAG 3' (antisense to bases 849 to 870)
WH6 = 5' GTG GAG AGT GCA GGT TCG GCCA 3' (antisense to bases 939 to 960)
WH7 = 5' TGA TGT CCA GGT TGT CTT AGA AG 3' (antisense to bases 447 to 466)
WH8 = 5' GAC CTG GGA GAG TGC AGG TG 3' (antisense to bases 769 to 788)
WH9 = 5' GGT ACG CGG AGC CGG GTC GG 3' (antisense to bases 942 to 961)
WH10 = 5' CGC ACG GCG GCG AGC GCG TC 3' (antisense to bases 41 to 60)
WH11 = 5' AAG GCA TCT ATT CTC ACG GC 3' (antisense to bases 67 to 86)
WH12 = 5' GCA TCT ATT CTC ACG GTC TG 3' (antisense to bases 560 to 579)
WH13 = 5' CAT CTA TTC TCA CGG TCT G 3' (antisense to bases 560 to 578)
WH14 = 5' TCT ATT CTC ACG GTC TG 3' (antisense to bases 560 to 576)

FIG. 19

INHIBITORS OF ENDOTHELIN-1 SYNTHESIS

FIELD OF THE INVENTION

The invention relates to sequences in human preproendothelin-1 mRNA against which antisense oligonucleotides can be used to inhibit the synthesis of endothelin-1. The invention also relates to the treatment for diseases where an excess production of endothelin-1 is an underlying cause of the symptoms.

BACKGROUND OF THE INVENTION

Endothelin-1 (ET-1) is a 21 amino acid peptide isolated from the conditioned medium of cultured endothelial cells. Subsequent studies have shown it to be synthesised in endothelial cells, epithelial cells, and both vascular and non-vascular smooth muscle cells. It is the most potent vasoconstrictor agent ever identified, and causes vasoconstriction in most if not all vascular beds. Endothelin-1 has a number of other actions, including promoting smooth muscle mitogenesis, which may be of equal or greater importance in the underlying pathological processes of a variety of diseases (Hayes and Webb, 1998).

The acute actions of endothelin-1 in the airways and in the pulmonary vasculature include pulmonary arterial and venous vasoconstriction, extravasation and oedema formation, and bronchoconstriction. However, current evidence suggests that when expression of endothelin-1 is upregulated, its involvement in chronic changes may be just as important as any acute vasoconstrictor effect. This is particularly true for the pulmonary vasculature and airways where endothelin-1 may have a long-term role in remodeling by promoting vascular and tracheal smooth muscle mitogenesis, and stimulating collagen synthesis by pulmonary fibroblasts.

Current approaches to inhibiting ET-1 have focused mainly on development of antagonists but these may have systemic effects that are detrimental to the pulmonary circulation (e.g. peripheral hypotension). In addition there are at least two endothelin receptor subtypes—namely, endothelin-A (ETA) subtype and endothelin-B (ETB) subtype. Both appear to be involved in mediating the vasoconstrictor responses to endothelin in the pulmonary vasculature (McCulloch et al., 1998). But the endothelin-B subtype is also a clearance receptor so agents blocking it increase circulating ET-1 levels (Loffler et al., 1993, and Fukuroda et al., 1994) and may reduce the effectiveness of the antagonism.

SUMMARY OF THE INVENTION

The present invention relates to antisense oligonucleotides that are complementary to human preproendothelin-1 mRNA and inhibit the synthesis of preproendothelin-1 and thereby endothelin-1; methods of inhibiting endothelin-1 synthesis; methods of inhibiting preproendothelin-1 synthesis; methods of administering antisense oligonucleotides to individuals for the purpose of inhibiting the synthesis of endothelin-1 and/or preproendothelin-1 and pharmaceutical compositions comprising one or more antisense oligonucleotides that bind to endothelin-1 and/or preproendothelin-1 mRNA. The present invention also relates to the treatment of diseases that are caused or aggravated by endothelin-1 production.

An embodiment of the present invention is an antisense oligonucleotide complementary to human preproendothelin-1 mRNA, wherein said oligonucleotide can inhibit the synthesis and/or release of human preproendothelin-1.

A preferred embodiment of the present invention is an antisense oligonucleotide that comprises any oligonucleotide complementary to the 5' untranslated region of human preproendothelin-1 mRNA, wherein the oligonucleotide can inhibit the synthesis of human preproendothelin-1. A preferred embodiment of the invention is an antisense oligonucleotide complementary to human preproendothelin-1 mRNA, comprising at least 12 nucleotide bases complementary to the 5' untranslated region of this mRNA, or an oligonucleotide that differs from said oligonucleotide by up to 3 nucleotides, or a derivative of said oligonucleotide.

Another preferred embodiment of the invention is an antisense oligonucleotide complementary to human preproendothelin-1 mRNA, consisting of from 12 to 32 bases and having at least 10 consecutive bases in common with S1 (SEQID No: 3), or an oligonucleotide that differs from said oligonucleotide by up to 3 nucleotides, or a derivative of said oligonucleotide.

Another preferred embodiment of the invention is an antisense oligonucleotide complementary to human preproendothelin-1 mRNA, consisting of from 12 to 32 bases and having at least 10 consecutive bases in common with S8 (SEQID No: 10) or an oligonucleotide that differs from said oligonucleotide by up to 3 nucleotides, or a derivative of said oligonucleotide.

Another preferred embodiment of the invention is an antisense oligonucleotide complementary to human preproendothelin-1 mRNA, consisting of from 12 to 32 bases and having at least 10 consecutive bases in common with WH10 (SEQID No: 20), or an oligonucleotide that differs from said oligonucleotide by up to 3 nucleotides, or a derivative of said oligonucleotide.

Yet another preferred embodiment of the invention is an antisense oligonucleotide complementary to human preproendothelin-1 mRNA, consisting of from 12 to 32 bases and having at least 10 consecutive bases in common with WH11 (SEQID No: 21), or an oligonucleotide that differs from said oligonucleotide by up to 3 nucleotides, or a derivative of said oligonucleotide.

Another preferred embodiment of the invention is an antisense oligonucleotide complementary to human preproendothelin-1 mRNA, consisting of from 12 to 32 bases and having at least 10 consecutive bases in common with WH20 (SEQID No: 38) or WH21 (SEQID No: 39, or an oligonucleotide that differs from said oligonucleotide by up to 3 nucleotides, or a derivative of said oligonucleotide.

Yet another preferred embodiment of the invention is an antisense oligonucleotide complementary to human preproendothelin-1 mRNA, consisting of from 12 to 32 bases and having at least 10 consecutive bases in common with WH29 (SEQID No: 56), or an oligonucleotide that differs from said oligonucleotide by up to 3 nucleotides, or a derivative of said oligonucleotide.

Another preferred embodiment of the invention is an antisense oligonucleotide complementary to human preproendothelin-1 mRNA, consisting of from 12 to 32 bases and having at least 10 consecutive bases in common with WH31 (SEQID No: 59), or an oligonucleotide that differs from said oligonucleotide by up to 3 nucleotides, or a derivative of said oligonucleotide.

Still another preferred embodiment of the present invention is an antisense oligonucleotide complementary to human preproendothelin-1 mRNA comprising an oligonucleotide selected from the group consisting of S1 (SEQID No: 3), S2 (SEQID No: 4), S3 (SEQID No: 5), S4 (SEQID No: 6), S5 (SEQID No: 7), S6 (SEQID No: 8), S7 (SEQID No: 9), S8 (SEQID No: 10), WH1 (SEQID No: 11), WH2 (SEQID No:

12), WH3 (SEQID No: 13), WH4 (SEQID No: 14), WH5 (SEQID No: 15), WH6 (SEQID No: 16), WH7 (SEQID No: 17), WH8 (SEQID No: 18), WH9 (SEQID No: 19), WH10 (SEQID No: 20), WH11 (SEQID No: 21), WH12 (SEQID No: 22), WH13 (SEQID No: 23), WH14 (SEQID No: 24), WH20 (SEQID No: 38), WH21 (SEQID No: 39), WH22 (SEQID No: 40), WH23 (SEQID No: 41), WH24 (SEQID No: 42), WH25 (SEQID No: 43), WH26 (SEQID No: 52), WH27 (SEQID No: 54), WH28 (SEQID No: 55), WH29 (SEQID No: 56), WH30(SEQID No: 57), WH31 (SEQID No: 59), WH32 (SEQID No: 60), WH33 (SEQID No: 61), WH34, WH35, WH36, WH37, WH38, WH39 and WH41 or an oligonucleotide that differs from said oligonucleotide by up to 3 nucleotides, or a derivative of said oligonucleotide.

Another preferred embodiment of the present invention is an antisense oligonucleotide complementary to human preproendothelin-1 mRNA comprising an oligonucleotide selected from the group consisting of S1A (SEQID No: 46), S1B (SEQID No: 47), WH10A (SEQID No: 28), WH11B (SEQID No: 31), WH11A (SEQID No: 29), WH11B (SEQID No: 31), WH20A, WH20B, WH20C, WH21A, WH21B, WH29A, WH29B, WH31A and WH31B or an oligonucleotide that differs from said oligonucleotide by up to 3 nucleotides, or a derivative of said oligonucleotide Another preferred embodiment of the invention is a method of reducing endothelin-1 synthesis in a patient in need of such treatment, comprising administering a pharmaceutically effective amount of a composition comprising at least one antisense oligonucleotide that binds to preproendothelin-1 mRNA.

Still another preferred embodiment of the invention is a pharmaceutical composition comprising a pharmaceutically effective amount of at least one antisense oligonucleotide that binds to endothelin-1 and/or preproendothelin-1 mRNA.

Figure 13:
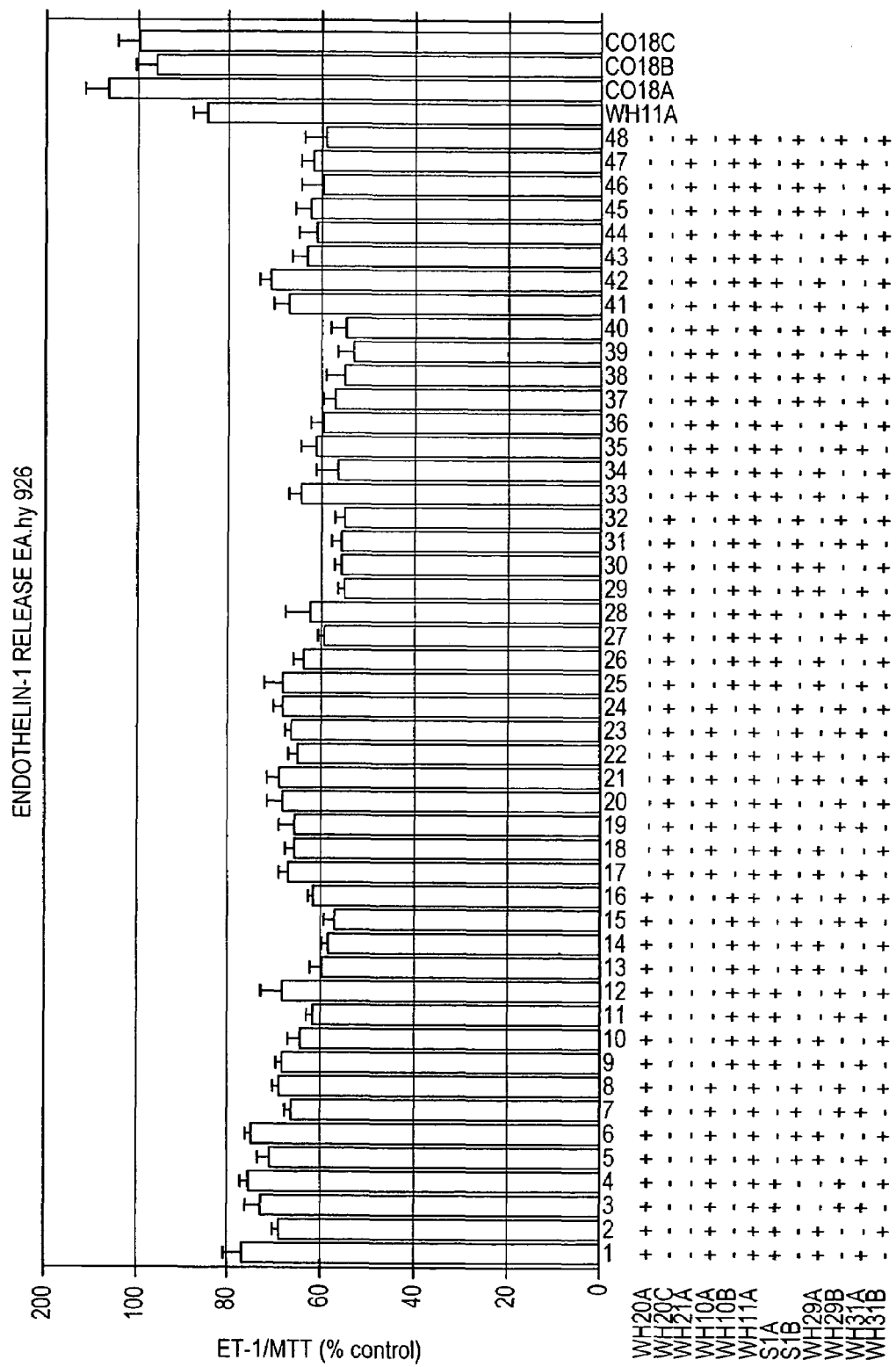

FIG. 13 shows effect of different ASON combinations (25 nM of each ASON, total 150 nM) on ET-1 release from EA.hy 926 cells. Comparison with 150 nM WH11A or 150 nM control ASONs.

Figure 14:
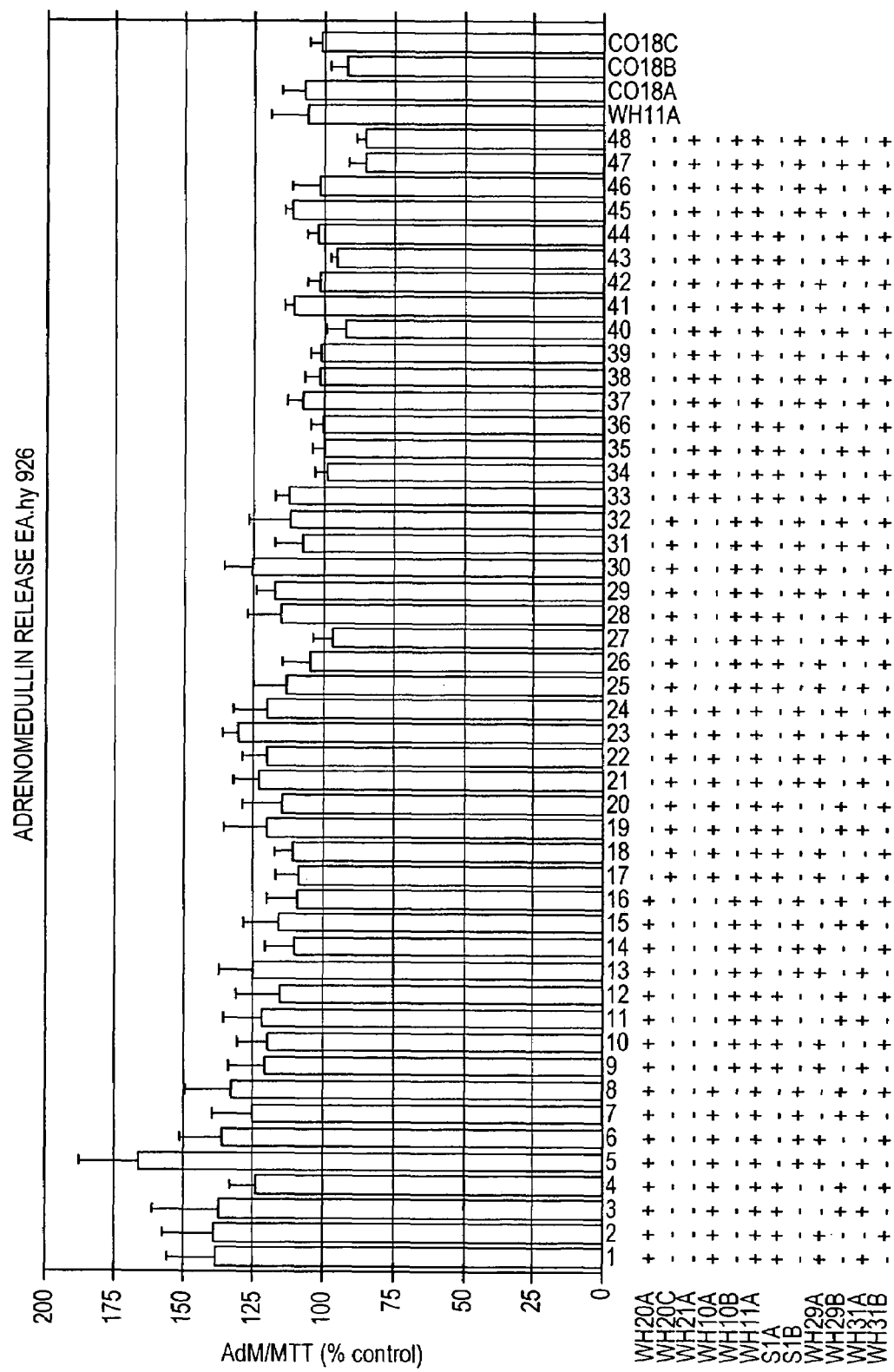

FIG. 14 shows effect of different ASON combinations (25 nM of each ASON, total 150 nM) on adrenomedullin release from EA.hy 926 cells. Comparison with 150 nM WH11A or 150 nM control ASONs.

Figure 15:
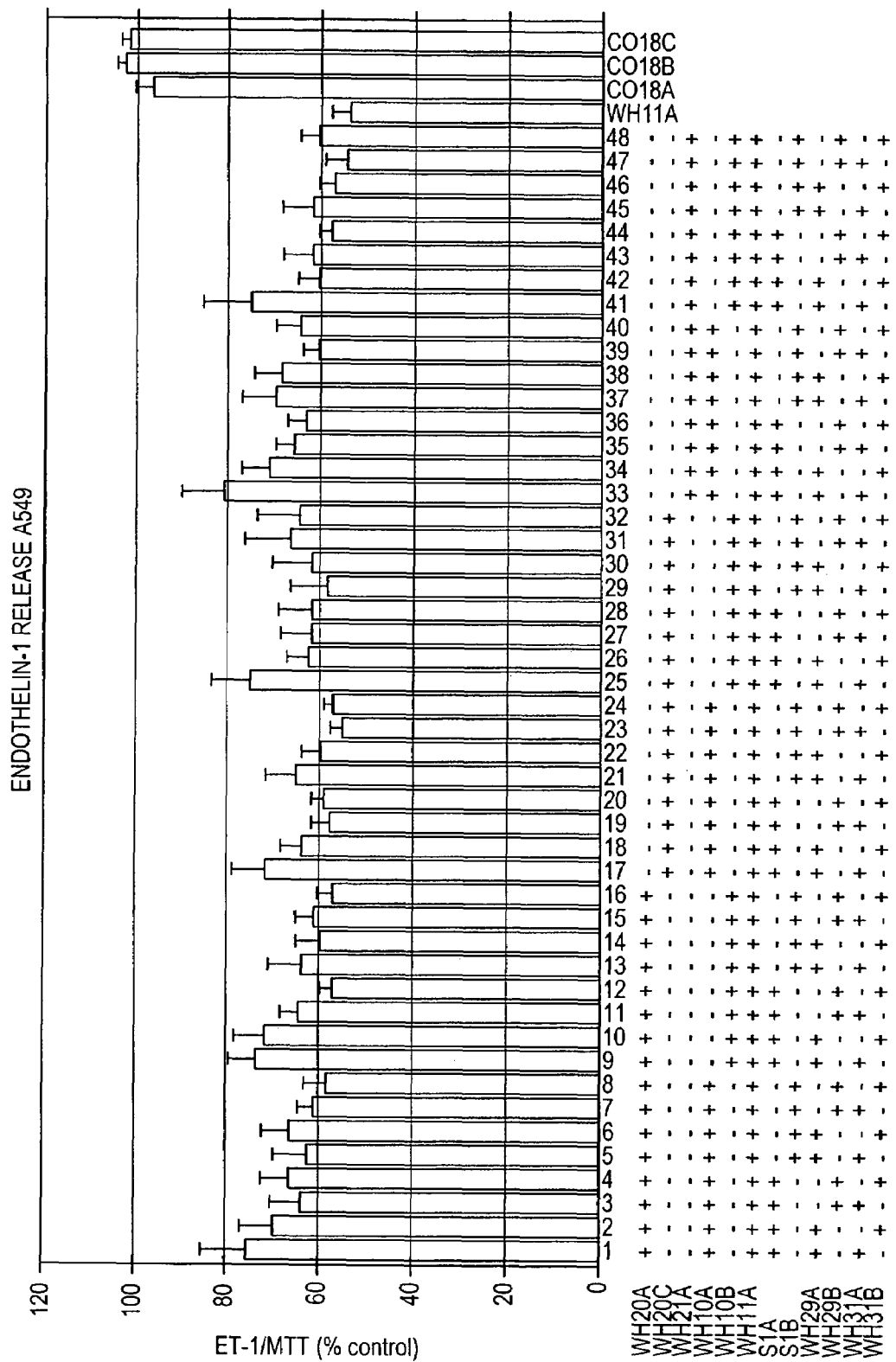

FIG. 15 shows effect of different ASON combinations (25 nM of each ASON, total 150 nM) on ET-1 release from A549 cells. Comparison with 150 nM WH11A or 150 nM control ASONs.

Figure 16:
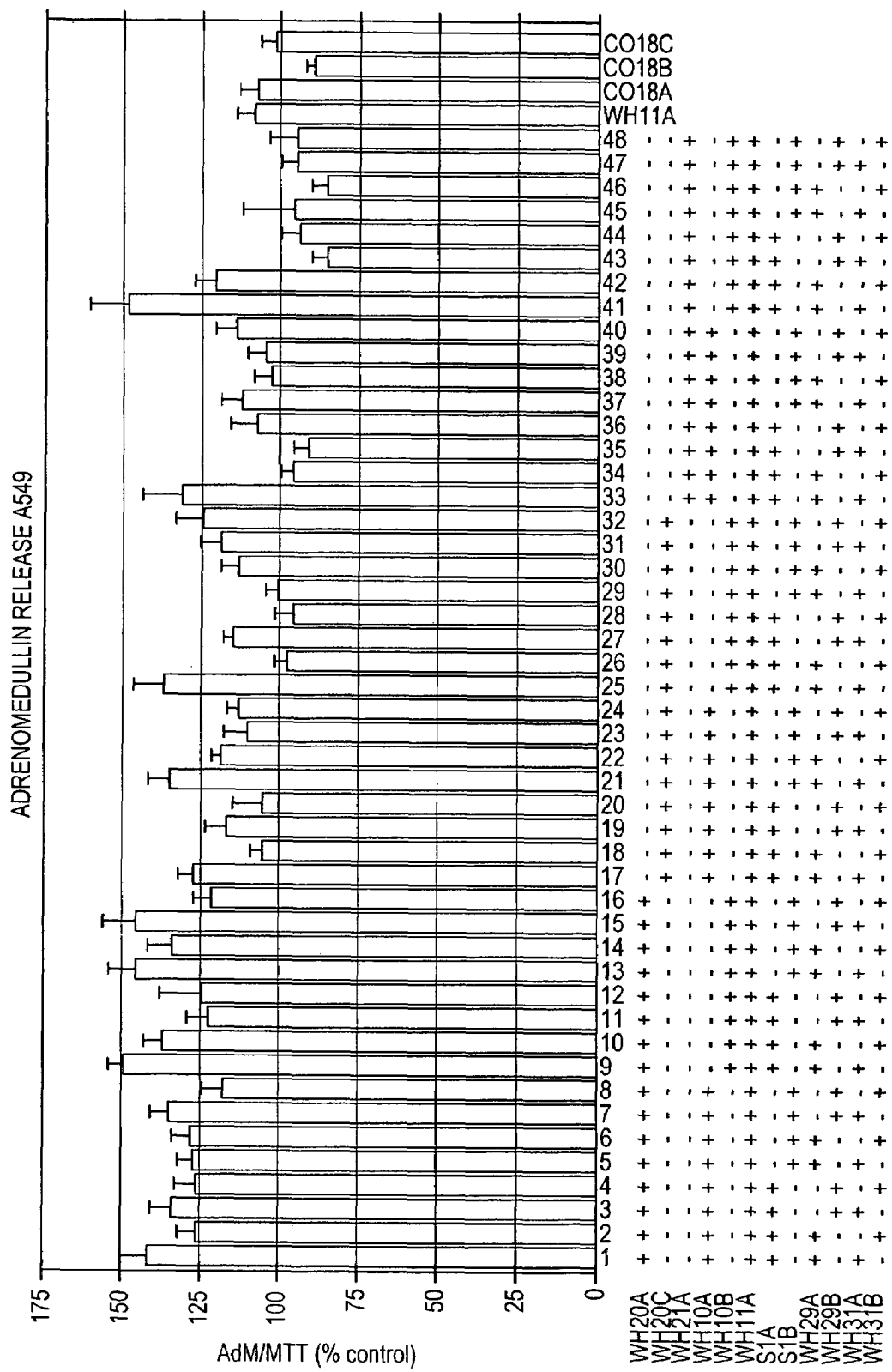

FIG. 16 shows effect of different ASON combinations (25 nM of each ASON, total 150 nM) on adrenomedullin release from A549 cells. Comparison with 150 nM WH11A or 150 nM control ASONs.

FIG. 17 illustrates various ASONs according to the invention, including the sequences of WH10 (SEQID No: 20), WH10A (SEQID No: 28), WH10B (SEQID No:30), WH10C (SEQID No:62), WH10D (SEQID No:63), WH10E (SEQID No. 64), WH11 (SEQID No: 21), WH11A (SEQID No: 29), WH11B (SEQID No: 31), WH11C (SEQID No: 65), WH11D (SEQID No:66), WH11E (SEQID No:67), WH20 (SEQID No: 38), WH21 (SEQID No: 39), WH22 (SEQID No: 40), WH23 (SEQID No: 41), WH24 (SEQID No: 42), WH25 (SEQID No: 43), WH26 (SEQID No: 52), WH27 (SEQID No: 54), WH28 (SEQID No: 55), WH29 (SEQID No: 56), WH30 (SEQID No: 57), WH31 (SEQID No: 59), WH32 (SEQID No: 60), WH33 (SEQID No: 61), S1 (SEQID No: 3), S1A (SEQID No: 46). S1B (SEQID No: 47), S1C (SEQID No:68), S1D (SEQID No:69), S1E (SEQID No:70), S2 (SEQID No: 4), S8 (SEQID No: 10), FIG. 18 illustrates the amino acid and cDNA sequences based on preproendothelin-1 mRNA, SEQID No:2 and SEQID No: 1, respectively.

FIG. 19 illustrates various ASONs according to the invention, including the sequences of S1 (SEQID No: 3), S2 (SEQID No: 4), S3 (SEQID No: 5), S4 (SEQID No: 6), S5 (SEQID No: 7), S6 (SEQID No: 8), S7 (SEQID No: 9), S8 (SEQID No: 10), WH1 (SEQID No: 11), WH2 (SEQID No: 12), WH3 (SEQID No: 13), WH4 (SEQID No: 14), WH5 (SEQID No: 15), WH6 (SEQID No: 16), WH7 (SEQID No: 17), WH8 (SEQID No: 18), WH9 (SEQID No: 19). WH10 (SEQID No: 20), WH11 (SEQID No: 21), WH12 (SEQID No: 22), WH13 (SEQID No: 23), WH14 (SEQID No: 24).

DESCRIPTION OF THE PREFERRED EMBODIMENTS

As used in the herein specification and appended claims, unless otherwise indicated, the terms "oligonucleotide", "antisense oligonucleotide", or "ASON" (meaning antisense oligonucleotide) include both oligomers of ribonucleotide, i.e., oligoribonucleotides, and oligomers of deoxyribonucleotide, i.e., oligodeoxyribonucleotides (also referred to herein as "oligodeoxynucleotides"). Oligodeoxynucleotides are preferred.

As used herein, unless otherwise indicated, the term "oligonucleotide" also includes oligomers which may be large enough to be termed "polynucleotides".

Preferably, an antisense oligonucleotide is employed which is targeted to 5' untranslated region of human mRNA associated with preproendothelin-1. Persons of ordinary skill in the art will be aware that mRNA includes not only the coding region which carries the information to encode a protein using the three letter genetic code, but also associated ribonucleotides which form a region known as the translated region, the 3'-untranslated region, the 5'-cap region, intron regions and intron/exon or splice junction ribonucleotides. Thus, oligonucleotides may preferably be formulated which are targeted wholly or in part to these associated ribonucleotides. In other embodiments, the oligonucleotide is targeted to a translation initiation site (AUG codon) or sequences in the 3'-untranslated region of the human preproendothelin-1 mRNA. The oligonucleotide may target the initial RNA transcript as well as the mature mRNA. The functions of messenger RNA to be interfered with include all vital functions such as translocation of the RNA to the site for protein translation, actual translation of protein from the RNA, splicing or maturation of the RNA and possibly even independent catalytic activity which may be engaged in by the RNA. The overall effect of such interference with the RNA function is to cause interference with preproendothelin-1 protein expression, and thereby inhibiting the synthesis of endothelin-1.

The term "correspond" means that the given compound has base pairing characteristics comparable to the nucleic acid sequence referred to, that is, comparable hybridization characteristics.

"Hybridization", in the context of this invention, means hydrogen bonding, also known as Watson-Crick base-pairing, between complementary bases, usually on opposite nucleic acid strands or two regions of a nucleic acid strand. Guanine and cytosine are examples of complementary bases which are known to form three hydrogen bonds between them. Adenine and thymine or adenine and uracil are examples of complementary bases which form two hydrogen bonds between them. "Specifically hybridizable" and "complementary" are terms used to indicate a sufficient degree of complementarity such that stable and specific binding occurs between the DNA and RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the previously uninfluenced function of the target molecule to cause a loss of its effectiveness, and there is a sufficient degree of being complementary to avoid non-specific binding of the oligonucleotide to non-target sequences under conditions in which specific binding is desired, i.e. under physiological conditions in the case of in vivo application or therapeutic treatment (or, in the case of in vitro assays, under conditions in which the assays are conducted).

Antisense oligonucleotides or oligonucleotide derivatives for combination according to the invention comprising nucleotide units or analogues/derivatives thereof sufficient in number and identity to allow hybridization preferably have a length that allows specific binding to the target sequence, especially a length corresponding to 12 to 42 nucleotide units, preferably to 15 to 32 nucleotide units, more preferably to 18 to 24, 18 to 22, 18 to 21, or 19 to 21 nucleotide units, and most preferably to 18 or 20 nucleotide units. Other antisense oligonucleotides that have 10, 11, 12, 13, 14, 15, 16, 17, 18, 19, 20 or more consecutive bases in common with the sequences of S1 (SEQID No: 3), S2 (SEQID No: 4), S3 (SEQID No: 5), S4 (SEQID No: 6), 55 (SEQID No: 7), S6 (SEQID No: 8), S7 (SEQID No: 9), S8 (SEQID No: 10), WH1 (SEQID No: 11), WH2 (SEQID No: 12), WH3 (SEQID No: 13), WH4 (SEQID No: 14), WH5 (SEQID No: 15), WH6 (SEQID No: 16), WH7 (SEQID No: 17), WH8 (SEQID No: 18), WH9 (SEQID No:

19), WH10 (SEQ ID No: 20), WH11 (SEQ ID No: 21), WH12 (SEQ ID No: 22), WH13 (SEQ ID No: 23), WH14 (SEQ ID No: 24), WH20 (SEQ ID No: 38), WH21 (SEQ ID No: 39), WH22 (SEQ ID No: 40), WH23 (SEQ ID No: 41), WH24 (SEQ ID No: 42), WH25 (SEQ ID No: 43), WH26 (SEQ ID No: 52), WH27 (SEQ ID No: 54), WH28 (SEQ ID No: 55), WH29 (SEQ ID No: 56), WH30 (SEQ ID No: 57), WH31 (SEQ ID No: 59), WH34, WH35, WH36, WH37, WH38, WH39, or WH41 are also in accordance with the invention. Antisense oligonucleotides that have 10, 11, 12, 13, 14, 15, 16, 17, 18, 19, 20 or more consecutive bases in common with the sequences of S1 (SEQ ID No: 3), WH10 (SEQ ID No: 20), or WH11 (SEQ ID No: 21) are more preferred.

Also, other antisense oligonucleotides that have 10, 11, 12, 13, 14, 15, 16, 17, 18 or more consecutive bases in common with the sequences of S1A (SEQ ID No: 46), S1B (SEQ ID No: 47), WH10A (SEQ ID No: 28), WH11B (SEQ ID No: 31), WH11A (SEQ ID No: 29), WH11B (SEQ ID No: 31), WH20A, WH20B, WH20C, WH21A, WH21B, WH29A, WH29B, WH31A or WH31B are in accordance with the invention. Antisense oligonucleotides that have 10, 11, 12, 13, 14, 15, 16, 17, 18, 19, 20 or more consecutive bases in common with the sequences of WH20A, WH20C, WH21A, WH29A, WH29B, WH31A or WH31B are more preferred.

The terms "oligonucleotide", "oligodeoxynucleotide", "antisense oligonucleotide" and "antisense oligodeoxynucleotide" include not only oligomers and polymers of the common biologically significant nucleotides, i.e., the nucleotides adenine ("A"), deoxyadenine ("dA"), guanine ("G"), deoxyguanine ("dG"), cytosine ("C"), deoxycytosine ("dC"), thymine ("T") and uracil ("U"), but also include oligomers and polymers hybridizable to the preproendothelin-1 mRNA transcript, which may contain other nucleotides such as 5-propynyluracil, 5-methylcytosine, 5-propynylcytosine, adenine, and 2-aminoadenine.

Likewise, the terms "oligonucleotide", "oligodeoxynucleotide", "antisense oligonucleotide", "antisense oligodeoxynucleotide", and "ASON" may include oligomers and polymers wherein one or more purine or pyrimidine moieties, sugar moieties or internucleotide linkages is chemically modified. This includes synthetic species derived from naturally occurring nucleotide subunits or their close homologues and may also refer to moieties which function similarly to naturally occurring oligonucleotides but which have non-naturally occurring portions, for example at least one building block that differs from the building blocks of a natural oligonucleotide. Thus, oligonucleotides with regard to their backbone may have altered sugar moieties and/or inter-sugar linkages, and, with regard to the bases, altered bases may be present. The term "oligonucleotide" is thus understood to also include oligomers which may properly be designated as "oligonucleosides" because of modification of the internucleotide phosphodiester bond. Such oligonucleotide "derivatives" are best described as being functionally interchangeable with natural oligonucleotides (or synthesized oligonucleotides along natural lines), but having one or more differences from natural structure. All such oligonucleotides are comprehended within this invention so long as they function effectively to show the hybridization properties to DNA or RNA deriving from preproendothelin-1, especially to the mRNA. Such modified oligonucleotides include, for example, the phosphorothioate oligonucleotides, discussed below.

The term "phosphorothioate oligonucleotide" means an oligonucleotide wherein one or more of the internucleotide linkages is a phosphorothioate group,

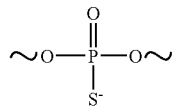

as opposed to the phosphodiester group

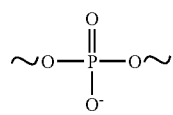

which is characteristic of unmodified oligonucleotides.

Phosphorothioate and in a broader sense includes other species such as phosphorodithioate, sulfate, sulfonate, sulfonamide, sulfone, sulfite, sulfoxide, sulfide, formacetal, 3'-thioformacetal, 5'-thioether, hydroxylamine (with $CH_2$—NH—O— $CH_2$ instead of the phosphodiester bond O→(HO—)P(.dbd.O)!—O—$CH_2$), methylene(methylimino) (with $CH_2$—N($CH_3$)—O—$CH_3$ instead of the phosphodiester bond); methyleneoxy (methylimino) (with $CH_2$—O—N($CH_3$)—$CH_2$ instead of the phosphodiester bond), methylene-((methylimino)-methylimino) (with $CH_2$—N($CH_3$)—N($CH_3$)—$CH_2$ instead of the phosphodiester bond), carbonate, 5'-N-carbamate, amide (with $CH_2$—(C.dbd.O)—NH—$CH_2$ instead of the phosphodiester bond, see International Application WO 92/20823), morpholino-carbamate (see Summerton, J. E. and Weller, D. D., U.S. Pat. No. 5,034,506) or peptide nucleic acid (see P. E. Nielsen, M. Egholm, R. H. Berg, O. Bucnardt, Science 254, 1497 (1991)) which are known for use in the art (for reviews with references concerning these modified nucleotides, see Milligan et al., J. Med. Chem. 36(14), 1923-37 (1993), and Uhlmann et al., Chemical Reviews 90(4), 543-84 (1990)). In accordance with some preferred embodiments, at least one of the phosphodiester bonds of the oligonucleotide has been substituted with a structure which functions to enhance the ability of the compositions to penetrate into the region of cells where the RNA or DNA whose activity to be modulated is located and in order to avoid extensive degradation of the oligonucleotide derivative due to nucleases that would result in ineffective cleavage products. It is preferred that such substitutions comprise phosphorothioate bonds, phosphorodithioate bonds, methyl phosphonate bonds, phosphoramidate bonds, amide bonds, boranophosphate bonds, phosphotriester bonds, short chain alkyl or cycloalkyl structures, or heteroatom-substituted short chain alkyl structures, and most especially phosphorothioate bonds or amide bonds.

By "alkylphosphonate oligonucleoside" is meant to be an oligonucleotide wherein one or more of the internucleotide linkages is an alkylphosphonate group,

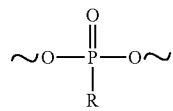

where R is an alkyl group preferably methyl or ethyl.

"Analogs" in reference to nucleosides includes synthetic nucleosides having modified base moieties and/or modified sugar moieties, e.g., described generally by Scheit, Nucleotide Analogs (John Wiley, New York, 1980). Such analogs include synthetic nucleosides designed to enhance binding properties, e.g., duplex or triplex stability, specificity, or the like.

The amino acid (SEQID No: 2) and cDNA sequence of human preproendothelin-1 mRNA (SEQID No: 2) is illustrated in FIG. 18, as disclosed in FEBS Lett. 231 (2), 440-444 (1988); the contents of which are hereby incorporated by reference. All number of the human preproendothelin-1 mRNA is based on the sequence numbering of the Genbank accession number Y00749, the contents of which are hereby incorporated by reference. The "5' untranslated region" or "5" untranslated region of human preproendothelin-1 mRNA" defines the bases of 1-253 of preproendothelin-1 mRNA.

The term "inhibit" means to reduce preproendothelin-1 synthesis, and therefore also to reduce the secretion or release of endothelin-1.

"EA.hy 926 cell line" means the cell line described by Edgell and colleagues [Edgell C -J. S., McDonald C C and Graham J P. Permanent cell line expressing human factor VIII-related antigen established by hybridization Pro. Natl. Acad. Sci. USA 1983, 80: 3734-3737]. This cell line was prepared by fusing human umbilical vein endothelial cells with A549 cells. A number of studies have shown that the resultant EA.hy 926 cell line retains characteristics of endothelial cells including synthesis of endothelin-1 [Corder R., Khan N. & Harrison V. J. A simple method for isolating human endothelin converting enzyme (ECE-1) free from contamination by neutral endopeptidase 24.11. Biochem. Biophys. Res. Comm. 1995, 207: 355-362].

"A549 cell line" means the cell line from the American Type Culture Collection (ATCC CCL-185). Originally derived from a human lung carcinoma, morphologically it displays epithelial-like characteristics.

The term "transfectant" means the reagent use to deliver the antisense oligonucleotides to cells. Generally composed of cationic lipid and neutral lipid, the transfectant forms liposomes with the oligonucleotides in aqueous solution. The resultant liposomes are the vehicle for transferring oligonucleotides into cells.

The term "remodeling" means a change in the structure of the airways or blood vessels, generally associated with an increase in smooth muscle cells either alone or combined with an increased level of the extracellular matrix. The term "obstructive airways disease" may also mean "chronic obstructive pulmonary disease".

One aspect of the present invention relates to one or more distinct antisense oligonucleotides that can bind to sequences of human preproendothelin-1 mRNA, and inhibit the synthesis of endothelin-1 mRNA. A combination of antisense oligonucleotides should allow the use of lower concentrations of each antisense oligonucleotide while retaining maximum inhibition of ET-1 synthesis. This may enable the total dose of antisense oligonucleotide to be increased while retaining a reduced probability of interference with the synthesis of unrelated proteins by genes with sequence homology. In a preferred embodiment, two, three, four or more antisense oligonucleotides are administered to a patient. Antisense oligonucleotides having shorter sequences are preferred for such combinations.

Another aspect of the present invention relates to reducing endothelin-1 in a patient whose disease is caused by or aggravated by excess production of endothelin-1. In a preferred embodiment of the invention, such diseases may include, but are not limited to pulmonary hypertension, obliterative bronchiolitis, chronic obstructive pulmonary disease, and asthma.

In another aspect of the invention, preproendothelin-1 one or more antisense oligonucleotides are administered to a patient to the lungs by inhalation. In a preferred embodiment, the antisense oligonucleotides are administered in an aerosolized form. In another preferred embodiment, the antisense oligonucleotides are administered as a dry powder.

In yet another aspect of the present invention, one or more of the antisense oligonucleotides are administered to a patient together with another drug that is for abrogating the underlying vasoconstrictor response. In one embodiment this other drug is a prostacyclin analogue. In a preferred embodiment, the antisense oligonucleotides are administered with a prostacyclin analogue to a patient with pulmonary hypertension.

Dosage Amounts, Forms, Frequency and Duration of Effect

Dosage amounts of the present invention include, but are not limited to from 0.01 to 50 mg/kg of vehicle with a pharmaceutically effective amount of antisense administered to the lungs as a dry powder or aerosol. Another embodiment of this include range is from 1 to 10 mg/kg.

The antisense oligonucleotides of the present invention may be applied to the lungs with varying frequency and for varying duration. In this regard, the skilled artisan will appreciate how to alter the frequency and duration of application to achieve the desired effect. For example, the antisense oligonucleotides of the instant invention can be taken at varying frequencies including on a daily basis, or 1 or more times daily. When being applied on a daily basis, the instant invention can be taken 1, 2, 3 or more times a day. The duration of treatment with the compositions of the instant invention can also vary. For example, the compositions may be applied for 1, 2, 3, 4, 5, 6 or more weeks; or for 1, 2, 3, 4, 5, 6 or more months. The duration of treatment may also be continuous. Again, the skilled artisan will appreciate the interaction between frequency and duration of use in order to achieve and/or maintain the desired effect.

In addition, the skilled artisan will appreciate how to vary concentrations of the instant invention in conjunction with the frequency and duration of use to achieve the desired effect. For example, the antisense oligonucleotides in a composition of higher concentration might be applied with less frequency or for a shorter duration. In contrast, antisense oligonucleotides of a lower concentration might be applied more frequently or for a longer duration.

In addition, the skilled artisan will appreciate how to vary the duration of the effective of the antisense oligonucleotides. The effective duration can be varied for the oligonucleotides so that they are effective for durations, such as, but not limited to, 1-48 hours, 4-24 hours, 6-18 hours, 4-18 hours or 6-12 hours.

Synthesis of Antisense Oligonucleotides

These ASONs were custom synthesised using standard methods on an automatic oligonucleotide synthesiser and then purified by high-performance liquid chromatography.

Cell Cultures Used for Testing

Testing of ASONs on cultured cells has been carried out using human endothelial (EA.hy 926 cell line) and epithelial (A549) cell lines. Cells were grown until they were 50 to 70% confluent, and then treated for 1 h in serum free medium containing the ASON at the concentrations indicated, optionally with an appropriate concentration of transfectant (Transfast, Promega). The cells were then returned to complete medium containing 10% fetal bovine serum for 4 h. At this point, the medium was replaced with serum free medium and the cells were incubated for 24 h to study ET-1 synthesis. In some studies the period with 10% fetal bovine serum was increased to 24 h and endothelin-1 synthesis was studied from 24 h-48 h. At the end of the incubation period, the conditioned medium was collected for subsequent ET-1 assay. To measure cell viability and non-specific cytotoxicity an MTT assay (an estimate of living cells based on mitochondrial dehydrogenase activity) was performed. ET-1 synthesis was measured by sensitive sandwich immunoassay and then for each well normalised to the MTT value. Statistical comparison was made with the effects of a control oligonucleotide by ANOVA with Fisher's LSD test. All studies have continued to compare the effects of the ASON on human endothelial (EA.hy 926 cell line) and epithelial (A549) cell lines following treatment of sub-confluent cultures with ASON in the presence of transfectant (Transfast, Promega).

After the initial evaluations (FIGS. 1-4), in order to design other active ASONs, the secondary structure of human pre-proET-1 mRNA was re-evaluated using "MFOLD" (the energy minimization program algorithm of Zuker). Based on this analysis, S1 (SEQID No: 3) was the only sequence where the 5' sequence was accessible for 3' binding of the ASON, Therefore, a number of new ASON were designed that also met this criteria (WH7 (SEQID No: 17) to WH14 (SEQID No: 24)). S8 (SEQID No: 10) is homologous to S1 (SEQID No: 3) moved one base 5' to see if this altered its activity as the secondary structure prediction indicated this might restrict its binding. From studies to identify target sequences to direct ASON against for inhibition of ET-1 synthesis, six regions of the 5'-non-coding sequence of preproendothelin-1 mRNA without any overlap (i.e. WH20 (SEQID No: 38)/21 (SEQID No: 39), WH10 (SEQID No: 20), WH11 (SEQID No: 21), S1 (SEQID No: 3), WH29 (SEQID No: 56) and WH31 (SEQID No: 59) have been defined. Evaluation of human genome database has so far not indicated these sequences are particularly homologous with other gene sequences suggesting they should be relatively free of non-specific effects.

Adrenomedullin Assay

A sensitive double-recognition site "sandwich" immunoassay for adrenomedullin has been developed so that it can be measured as a control gene in these studies. The assay is performed in a 96-well plate format using plates which are pre-coated with rabbit IgG specific for the N-terminal of adrenomedullin. The assay involves overnight incubation of sample or standard with biotinylated sheep IgG specific for the C-terminal of adrenomedullin. Bound C-terminal IgG is detected by performing a further incubation with $^{125}$I-streptavidin followed by counting. Bound $^{125}$I is proportional to the adrenomedullin concentration for which the assay range is 1 to 1000 fmol/ml.

Exon-intron Antisense Oligonucleotides

Figure 1:
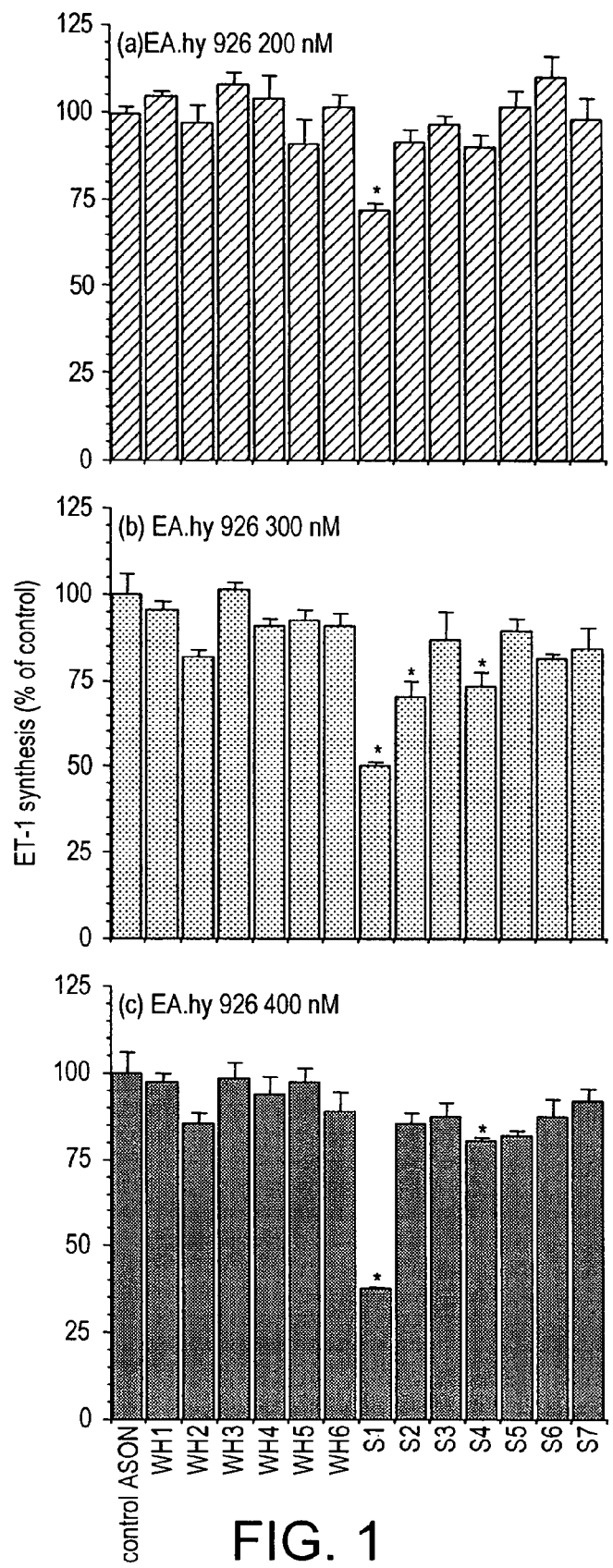
FIGS. 1(a)-1(c) illustrate the effect of (a) 200 nM, (b) 300 nM, and (c) 400 nM antisense oligonucleotide on ET-1 synthesis in the endothelial cell line EA.hy 926. Results are from two experiments with n=6 for each treatment. *indicates significantly reduced ET-1 synthesis p<0.001 compared to the values for the control antisense oligonucleotide. The x-axes of FIGS. 1(a) and 1(b) are identical to the x-axis of FIG. 1(c).
Figure 2:
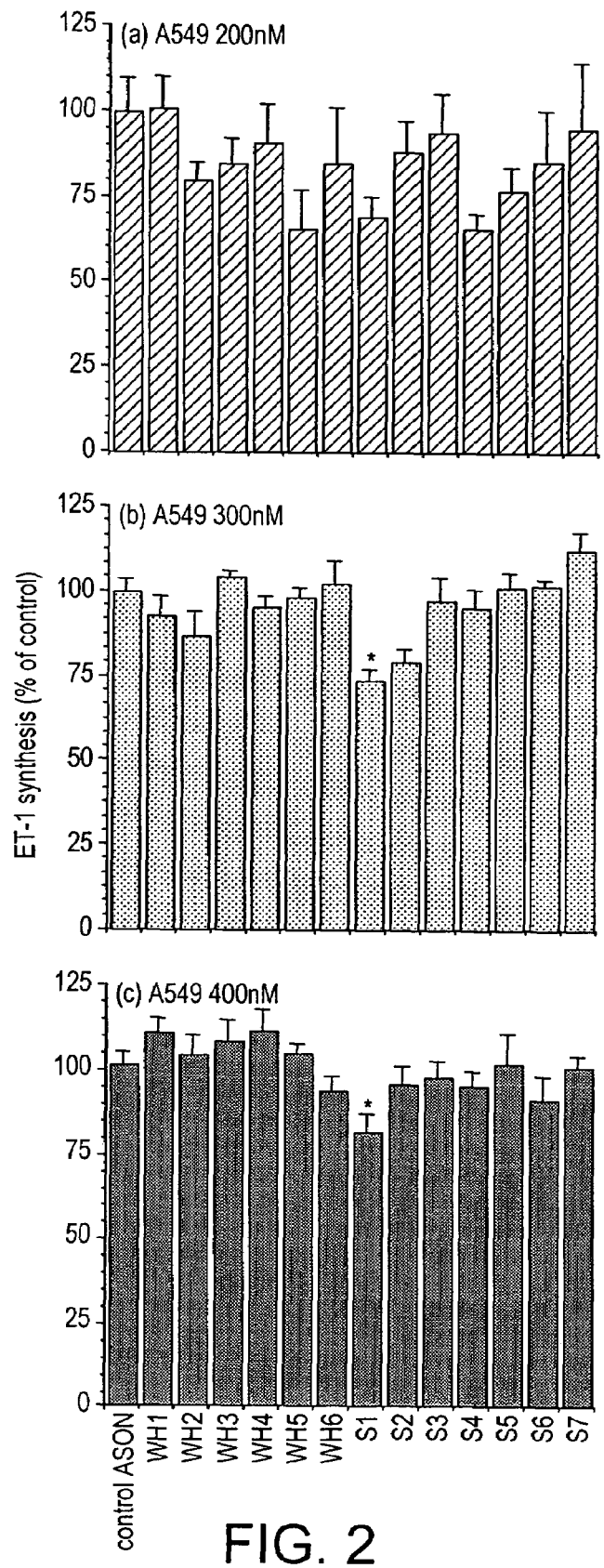
FIGS. 2(a)-2(c) illustrate the effect of (a) 200 nM, (b) 300 nM, and (c) 400 nM antisense oligonucleotide on ET-1 synthesis in the epithelial cell line A549. Results are from two experiments with n=6 for each treatment, except for (c) where n=9-11. * indicates significantly reduced ET-1 synthesis p<0.01 compared to the values for the control antisense oligonucleotide. The x-axes of FIGS. 2(a) and 2(b) are identical to the x-axis of FIG. 2(c).
Figure 3:
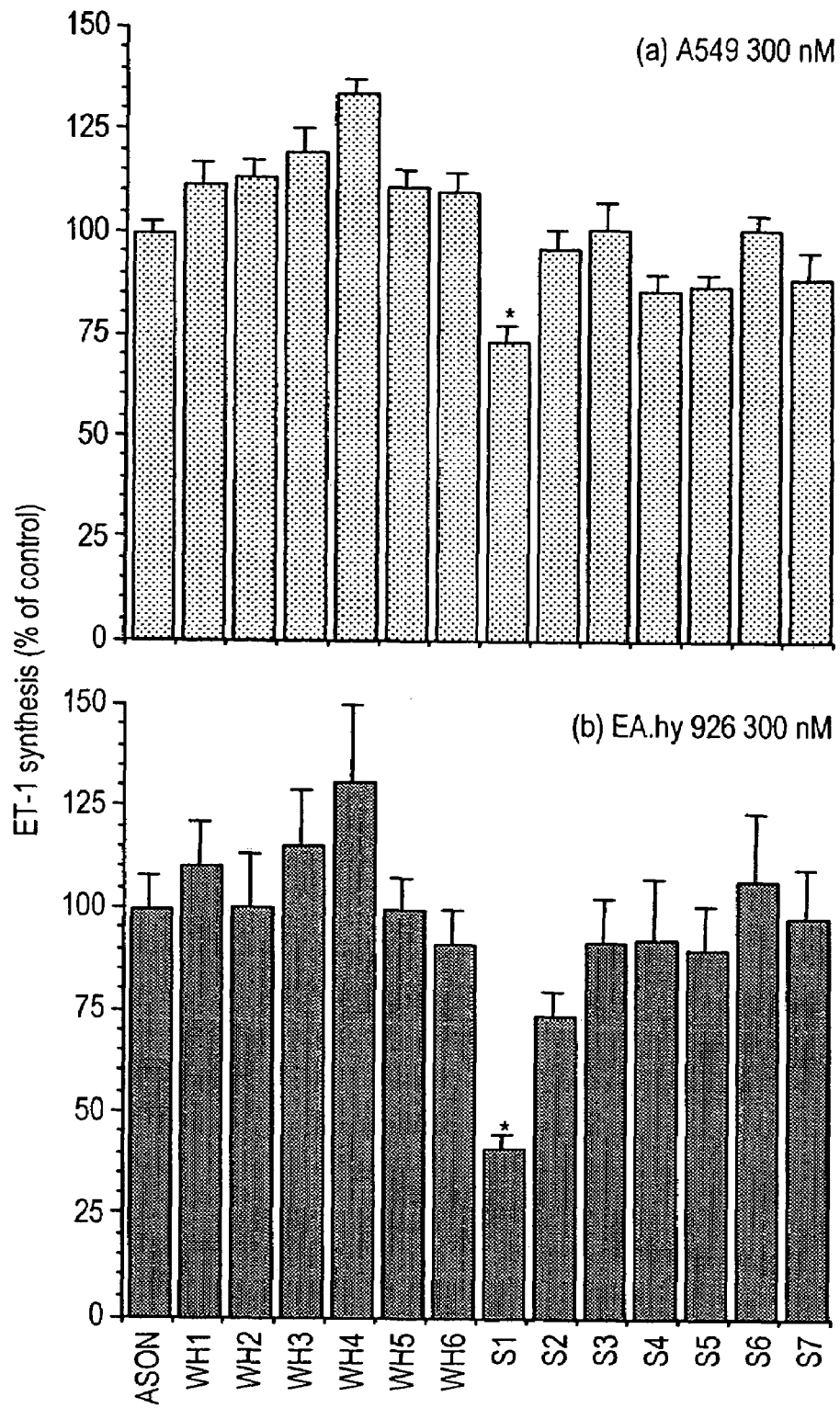
FIGS. 3(a)-3(b) illustrate the effect of 300 nM antisense oligonucleotide on ET-1 synthesis from 24-48 h after transfection in (a) A549 cells and (b) EA.hy 926 cells. After transfection with ASON cells were grown in complete medium containing 10% foetal bovine serum for 24 h prior to the study period. Results are from two experiments for A549 (n=8 for each) and from three experiments for EA.hy 926 (n=12 for each). *indicates significantly reduced ET-1 synthesis p<0.001 compared to the values for the control antisense oligonucleotide. The x-axis of FIG. 3(a) is identical to the x-axis of FIG. 3(b).
Figure 4:
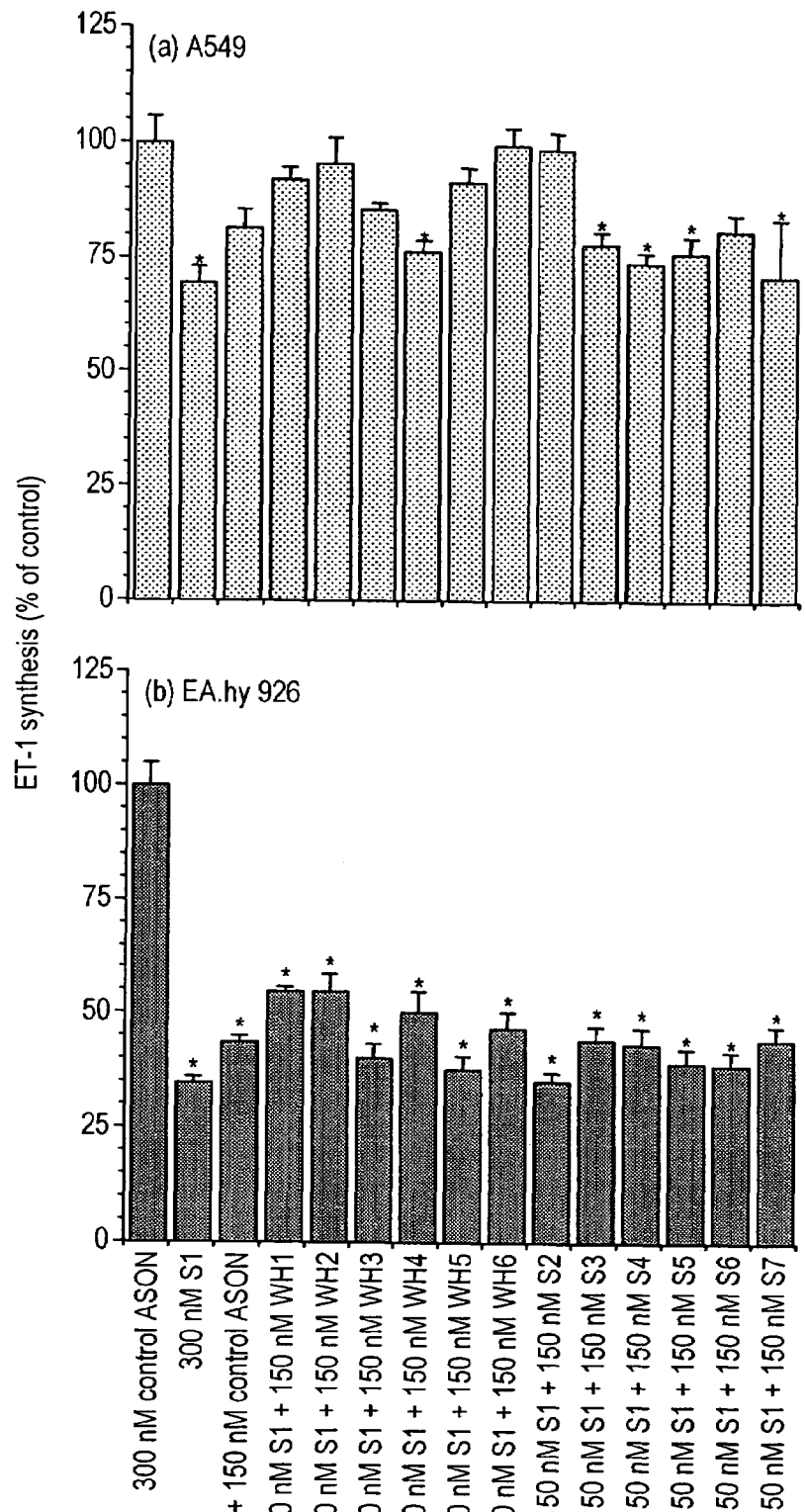
FIGS. 4(a)-4(b) illustrate the effect of combination of other antisense oligonucleotides with S1. The combined concentration of S1 with other oligonucleotides was 300 nM in each case. ET-1 synthesis was studied from 24-48 h after transfection in (a) A549 cells and (b) EA.hy 926 cells. Results are from two experiments for A549 and EA.hy 926 (n=8 for each). *indicates significantly reduced ET-1 synthesis p<0.001 compared to the values for the control antisense oligonucleotide alone. The x-axis of FIG. 4(a) is identical to the x-axis of FIG. 4(b).
Figure 5:
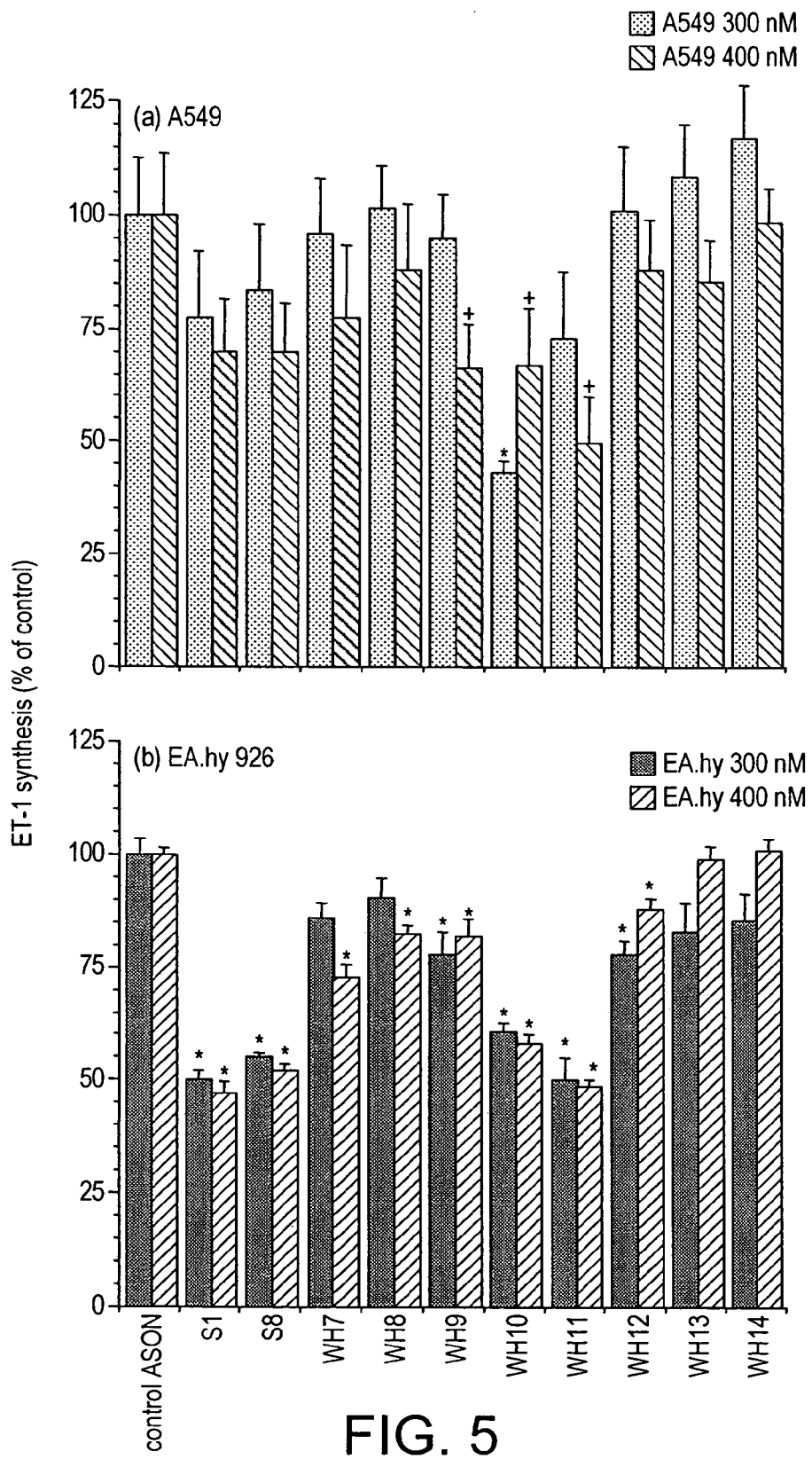
FIGS. 5(a)-5(b) illustrate the effect on ET-1 synthesis of new antisense oligonucleotides at 300 nM and 400 nM. Study period was first 24 h after transfection for (a) A549 cells and (b) EA.hy 926 cells. Results are from two experiments at each concentration for A549 and EA.hy 926 (n=6/7 for each treatment), *indicates significantly reduced ET-1 synthesis p<0.001, +=p<0.05 compared to the values for the control antisense oligonucleotide. The x-axis of FIG. 5(a) is identical to the x-axis of FIG. 5(b).
Figure 6:
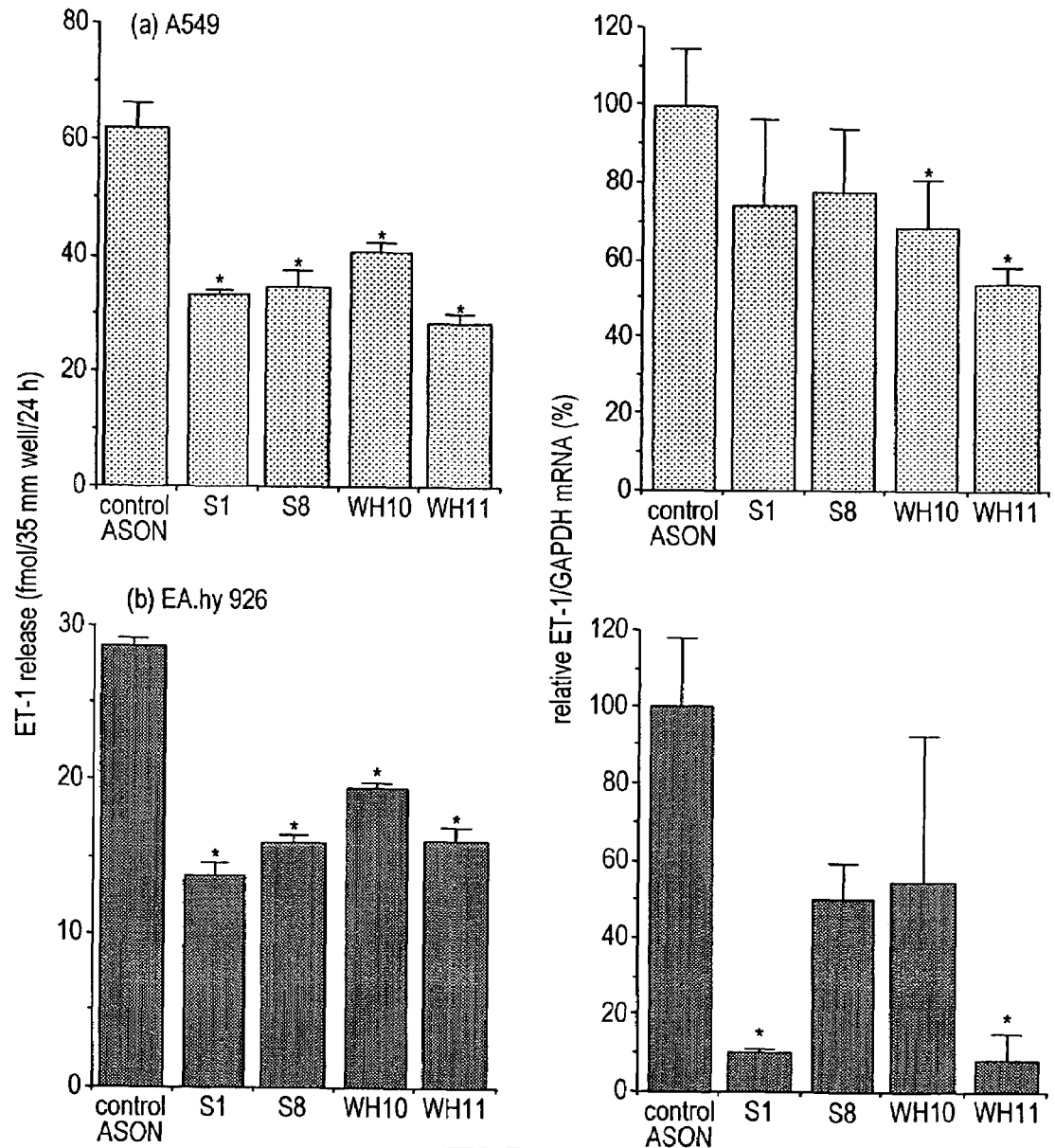
FIG. 6 shows effect of 400 nM antisense oligonucleotide on ET-1 synthesis measured over first 24 h after transfection in (a) A549 cells and (b) EA.hy 926 cells. Right hand panels show relative mRNA for preproendothelin-1/GAPDH from cells harvested at the end of the 24 h incubation period. Results are from one experiment for A549 and EA.hy (n=3 for each treatment), *indicates significant reductions p<0.05 compared to the values for the control, oligonucleotide.
Figure 7:
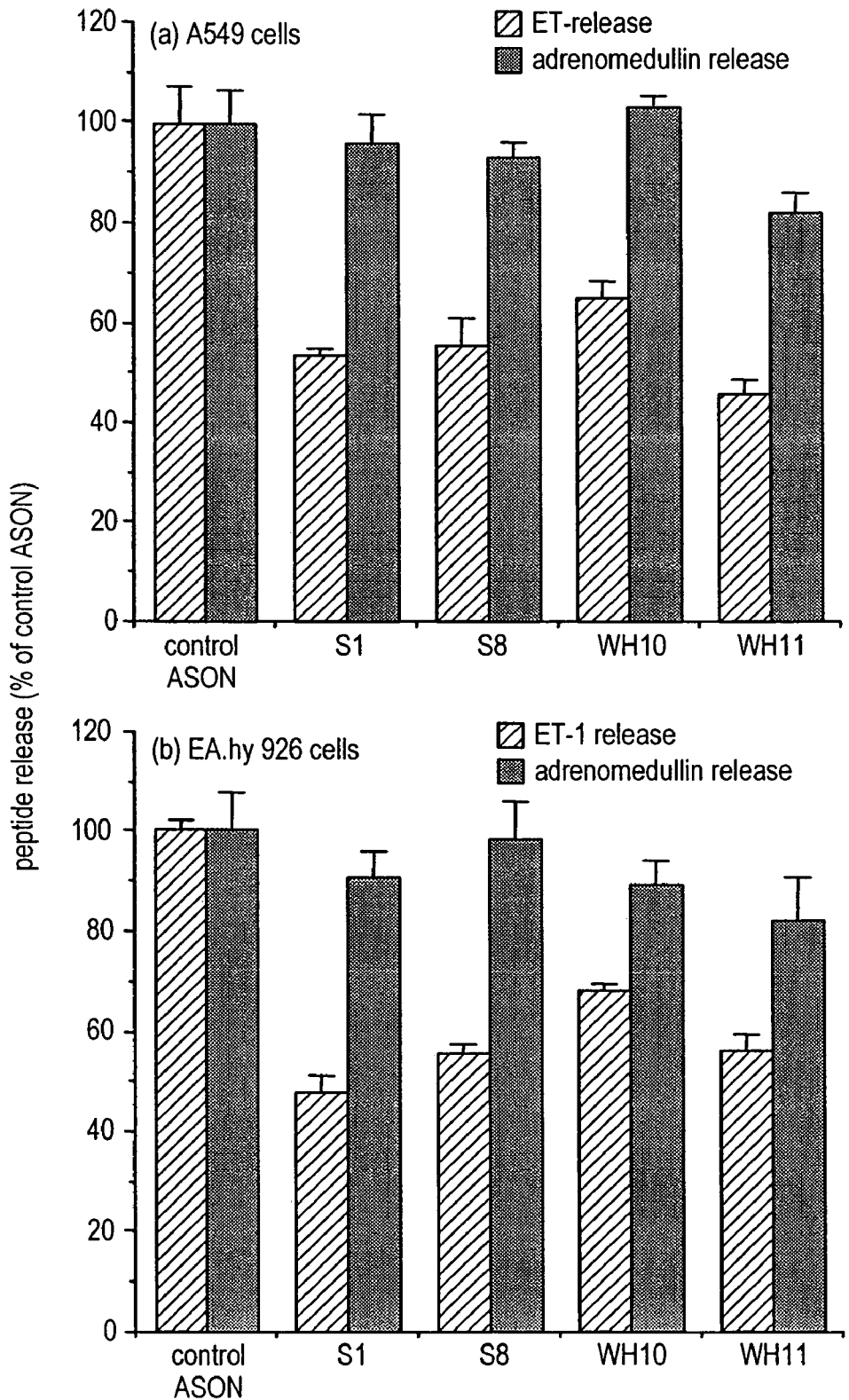
FIG. 7 is a comparison of the effect of 400 nM preproendothelin antisense oligonucleotides on ET-1 synthesis and adrenomedullin synthesis in (a) A549 cells and (b) EA.hy 926 cells. Values are expressed as a % of the release in the presence of a control antisense oligonucleotide.
Figure 8:
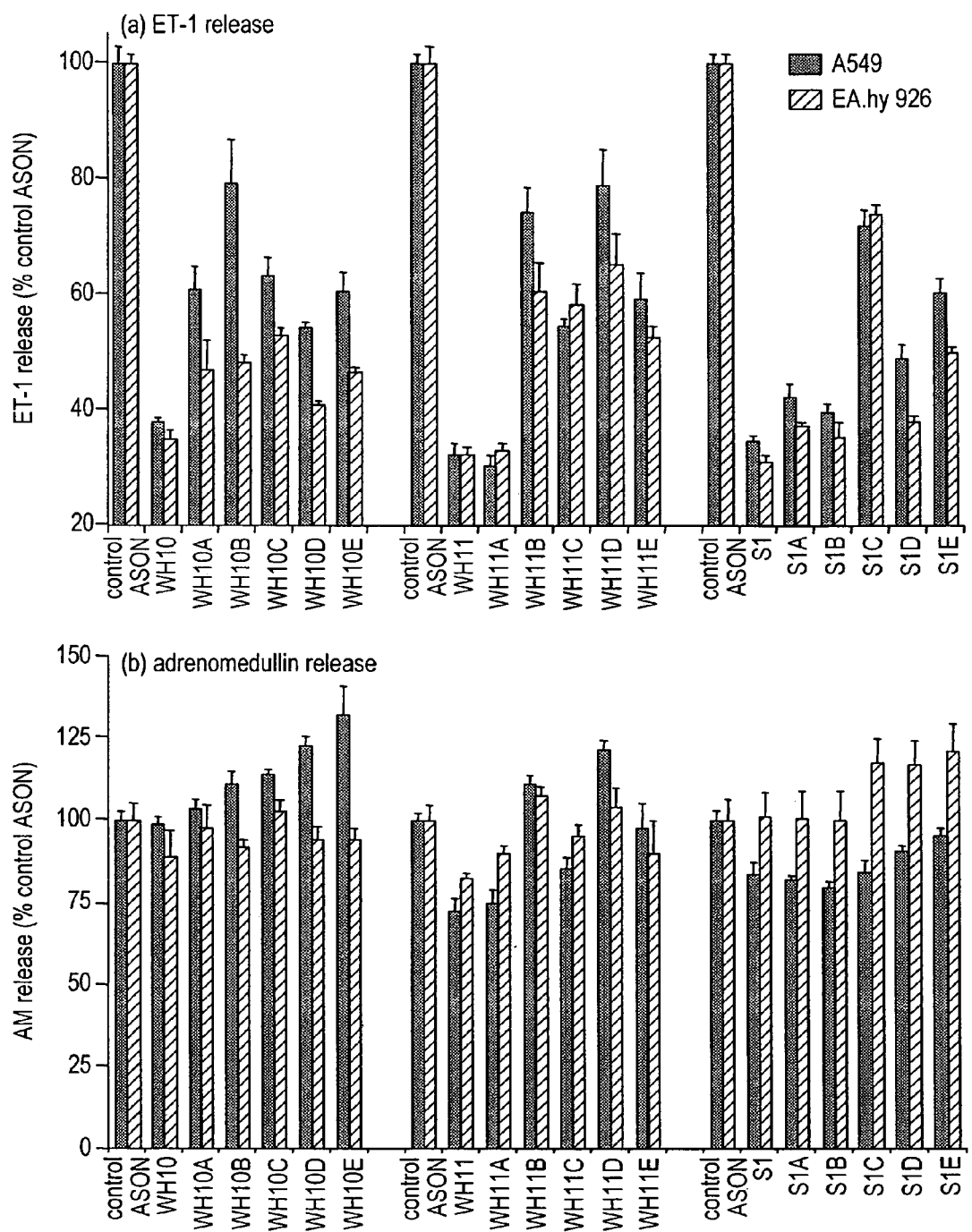
FIGS. 8(a)-8(b) show effect of modifying the length of the active phosphorothioate antisense oligonucleotides WH10, WH11 and S1 (20 mers). Comparison of ET-1 and adrenomedullin synthesis by A549 and EA.hy 926 cells. After transfection for 1 h, and 4 h recovery in complete medium, effects on ET-1 synthesis were determined over the following 24 h. Results are from two experiments (n=6 for each). A and B are 18 mers; C, D and E are 16 mers, all were tested at 300 nM.
Figure 9:
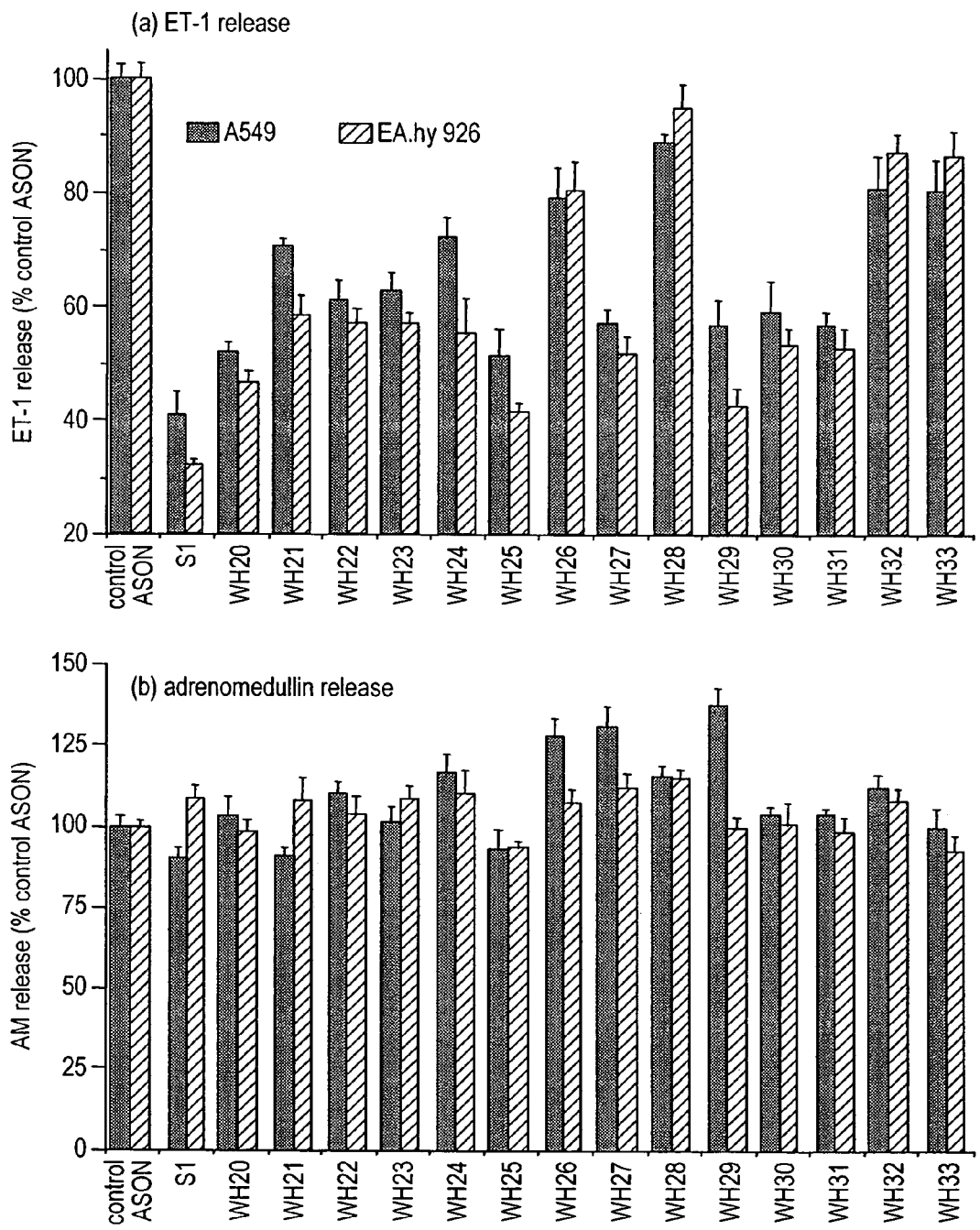
FIGS. 9(a)-9(b) show effect of phosphorothioate antisense oligonucleotides (300 nM) targeting the 5'-non-coding region of preproendothelin-1 mRNA. Significant reductions in ET-1 synthesis were obtained with both A549 and EA.hy 926 cells without altering adrenomedullin production. After transfection for 1 h, and 4 h recovery in complete medium, effects on ET-1 synthesis were determined over the following 24 h. Results are from two experiments (n=6 for each).

The effects of ASONs targeting exon-intron splice sites in the primary transcript of the preproendothelin-1 gene have been evaluated and compared with S1 (SEQID No: 3) (FIG. 4). The antisense oligonucleotides tested were WH34 (=3'-splice site of exon-1); (WH35=5'-splice site of exon-2); WH36 (=3-splice site of exon-2); WH37 (=5'-splice site of exon-3); WH38 (3' splice site of exon-3); WH39 (=5'-splice site of exon4); WH40(=3' splice site of exon4) and WH41 (=5' splice site of exon-5). After transfection for 1 h, and 4 h recovery in complete medium, effects on ET-1 synthesis were determined over the following 24 h.

WH34, WH35, WH36, WH37, WH38, WH39 and WH41 showed significant inhibition of ET-1 synthesis without significantly reducing adrenomedullin synthesis. These results suggest that the target for ASON molecules includes primary RNA transcripts prior to processing to mRNA, as well as the mRNA itself.

Effect of Combinations of ASONs on Reductions in ET-1 Synthesis

Test (A)

Figure 10:
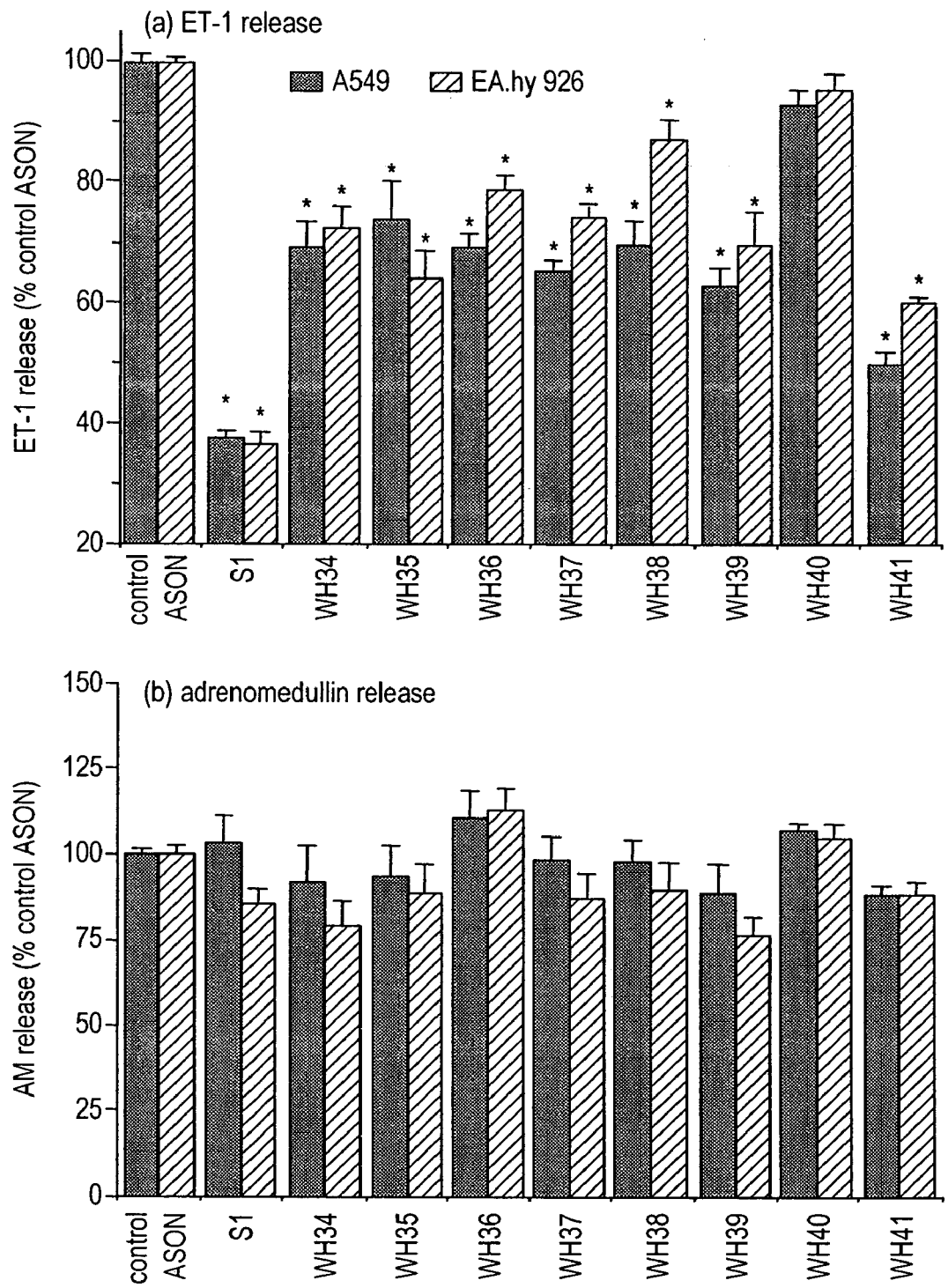
FIGS. 10(a)-10(b) show effect of phosphorothioate antisense oligonucleotides (300 nM) targeting exon-intron splice sites of the primary RNA transcript of preproendothelin-1. Comparison of ET-1 and adrenomedullin synthesis by A549 and EA. Hy 926 cells. After transfection for 1 h, and 4 h recovery in complete medium, effects on ET-1 synthesis were determined over the following 24 h. Results are from two experiments (n=6 for each). * indicates P<0.01 compared to control oligonucleotide.
Figure 11:
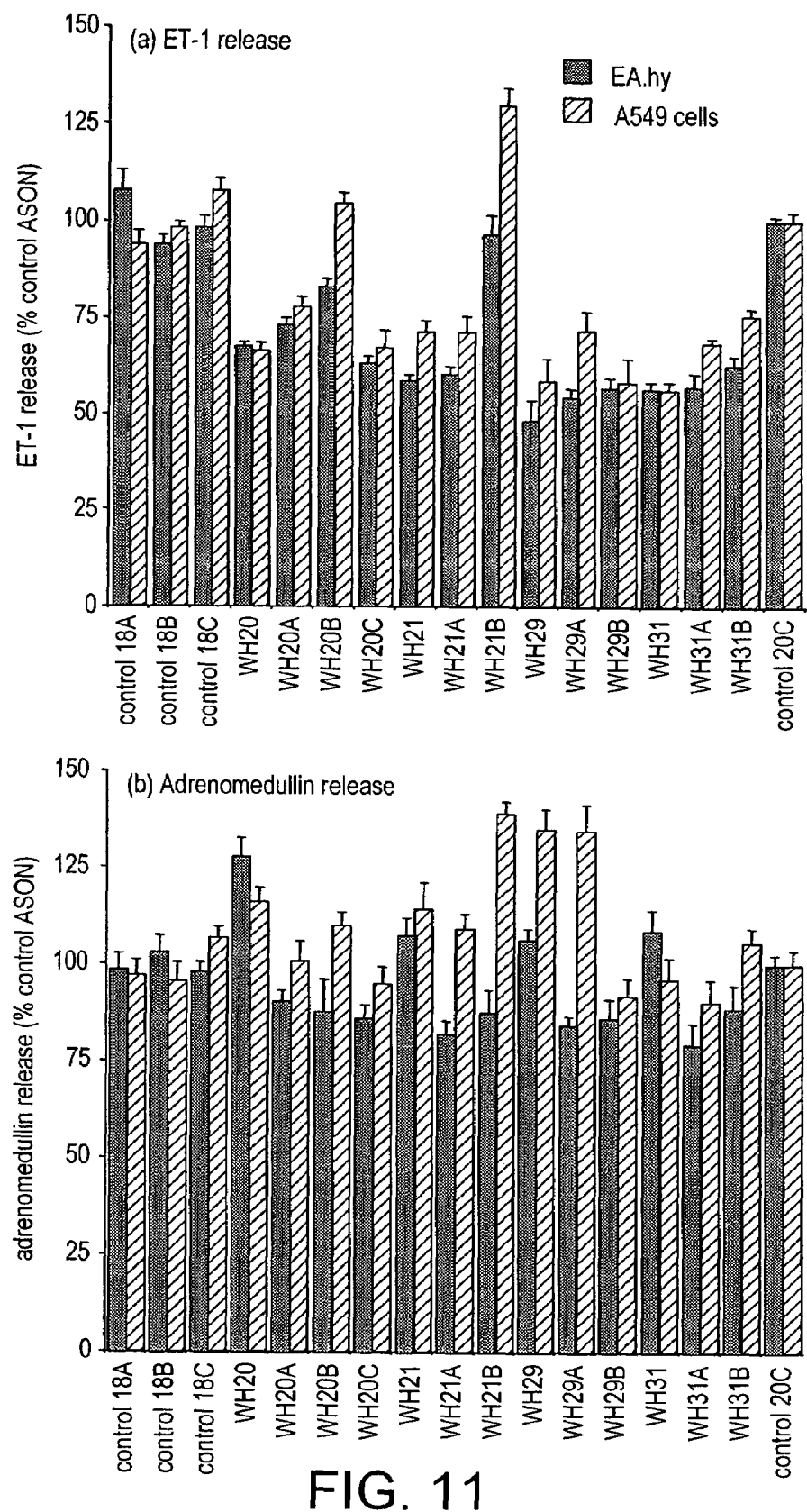
FIGS. 11(a)-11(b) show comparison of 18-mer phosphorothioate ASONs (WH20A, WH20B, WH20C, WH21A, WH21B, WH29A, WH29B, WH31A and WH31B) with corresponding 20-mer phosphorothioate ASONs (WH20, WH21, WH29 and WH31) on (a) ET-1 release and (b) adrenomedullin release from EA.hy 926 cells and A549 cells. The ASON concentration was 200 nM for each.
Figure 12:
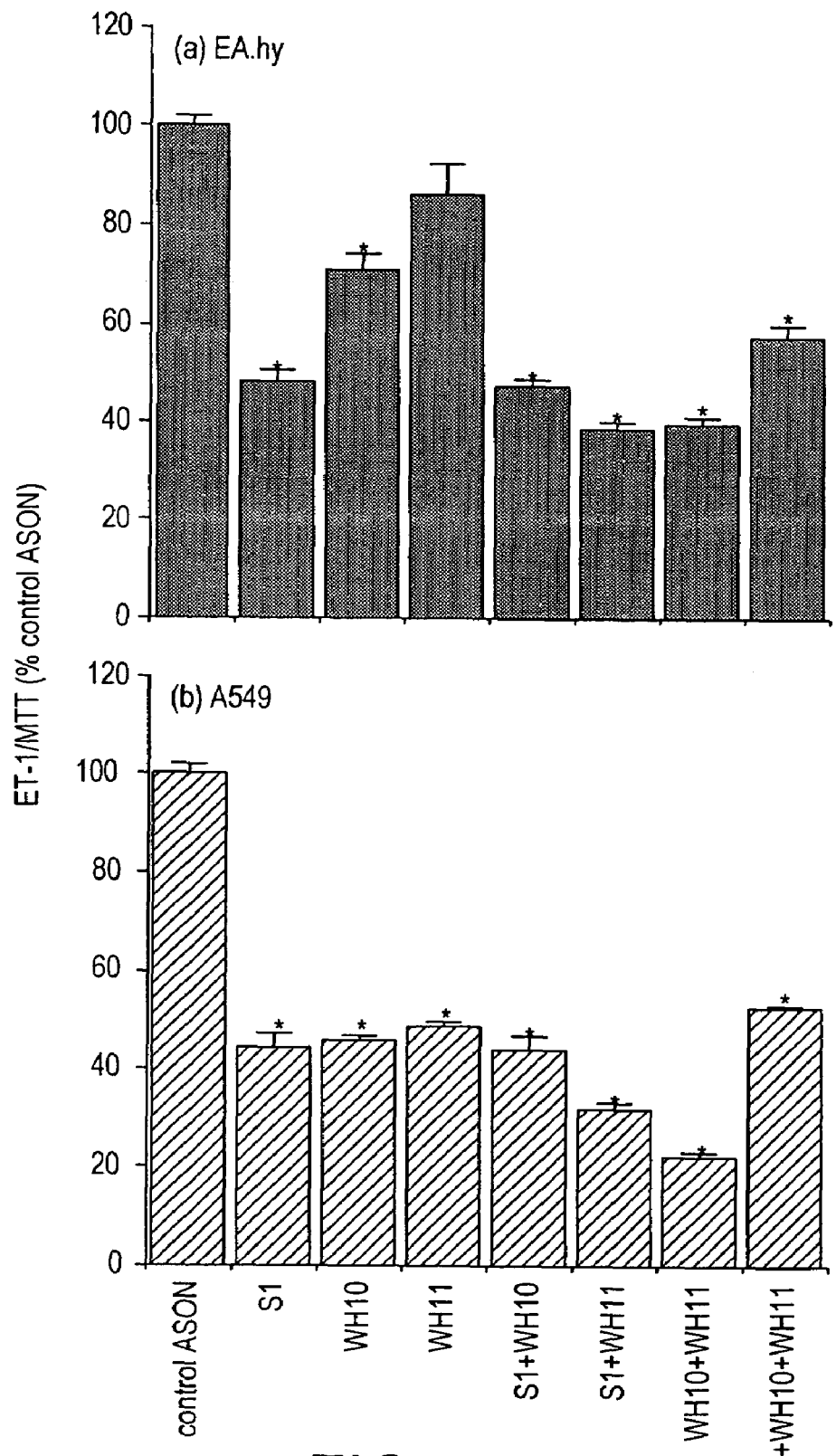
FIGS. 12(a)-12(b) show effect of ASONs alone or in combination on ET-1 synthesis by EA.hy 926 and A549 24-48 h after transfection with oligonucleotide. After transfection with ASON, cells were grown in complete medium containing 10% foetal bovine serum for 24 h prior to the study period. For each condition the final concentration is 300 nM phosphorothioate oligonucleotide, paired combinations are 150 nM of each, the triple combination is 100 nM of each. Results are n=6 for each. *indicates significantly reduced ET-1 synthesis compared to control ASON. The x-axis of FIG. 12(a) is identical to the x-axis of FIG. 12(b).

The active ASONs S1 (SEQID No: 3), WH10 (SEQID No: 20), and WH11 (SEQID No: 21) are all complementary to sequences in the 5' untranslated region of human preproET-1 mRNA. To test whether combination of different active ASONs could increase the degree of inhibition of ET-1 synthesis, the effects of combining of these ASONs were tested. The combinations tested were [S1 (SEQID No: 3) +WH10 (SEQID No: 20)], [WH10 (SEQID No: 20)+WH11 (SEQID No: 21)] and [S1 (SEQID No: 3) +WH10 (SEQID No: 20) +WH11 (SEQID No: 21). EA.hy 926 and A549 cells were transfected for 1 h with ASONs in the combinations indicated and then grown for 24 h in complete medium. ET-1 release was then studied from 24-48 h. The results suggest that combination of ASONs may be able to achieve a greater effect on ET-1 synthesis than use of individual ASONs (FIG. 10).

Test (B)

To evaluate whether the various ASON could be used as combinations, tests were performed on EA.hy 926 and A549 cells using the most effective 18-mer phosphorothioate ASONs which targeted six sequences of the 5'-nontranslated region of preproendothelin-1 mRNA. The simultaneous comparisons that were undertaken included assessing whether there were major differences in the inhibition of ET-1 synthesis for: WH20A v. WH20C v. WH21A; WH10A (SEQID No: 28) v. WH10B (SEQID No: 30); S1A (SEQID No: 46) v. S1B (SEQID No: 47); WH29A v. WH29B; or WH31A v. WH31B, WH11A (SEQID No: 29) was more effective in earlier experiments than WH11B (SEQID No: 31), therefore WH11A (SEQID No: 29) was selected for use in the comparison studies of combinations. These experiments compared combinations of 6 ASONs (25 nM of each) with 150 nM WH11A (SEQID No: 29), or 150 nM of three different 18 mer control ASONs. Comparison of the effectiveness of the different combinations on the release of ET-1 and the control gene (adrenomedullin) are shown in FIGS. 13 to 16. All combinations significantly inhibited ET-1 release. Although there was no combination which was significantly better on both cell types, statistical analysis showed on both cell lines that combinations with S1B (SEQID No: 47) and WH29B were significantly more effective than those with S1A (SEQID No: 46) and WH29A respectively. In addition WH10B (SEQID No: 30) containing combinations were more effective on EA.hy 926 cells than WH10A (SEQID No: 28), and WH20A was less effective than either WH20C or WH21A. Based on this analysis the most effective inhibition should be obtained with the following combinations:

[WH20C or WH21A+WH10B (SEQID No: 30)+WH11A (SEQID No: 29)+S1B (SEQID No: 47)+WH29B+WH31A or WH31B], which corresponds to combinations 31, 32, 47 and 48.

Lung and airways diseases can be treated with the antisense oligonucleotide inhibition of preproendothelin-1. These diseases include pulmonary hypertension, obliterative bronchiolitis, chronic obstructive pulmonary disease, and asthma.

Medical management of pulmonary hypertension (PH) has only a limited success, such that the associated cardiac changes and progressive vascular remodelling rapidly become life-threatening. Survival after diagnosis is generally less than 5 years. In recent years endothelial dysfunction and remodelling of the arterial vasculature have emerged as new targets for treatment in a variety of cardiovascular diseases. This is particularly true for pulmonary hypertension (PH), which, because of its refractoriness to current treatment, is in need of novel therapeutic approaches to control such changes (Marshall and Marshall, 1991, and Riley, 1991).

Irrespective of the cause, chronic pulmonary hypertension results in varying degrees of arterial remodeling with increased pulmonary vascular resistance and progressive right heart failure. In primary pulmonary hypertension increases in vascular resistance may initially be due to vasoconstriction but with time structural changes start to obstruct the pulmonary arteries causing further increases in vascular resistance and increasing the likelihood of right heart failure (Marshall and Marshall, 1991, and Riley, 1991). Remodeling involves both smooth muscle proliferation and the formation of extracellular matrix proteins (Marshall and Marshall, 1991, and Riley, 1991). Endothelin-1 has been implicated as a mediator of the vasoconstriction and it may also precipitate the remodelling (Hayes and Webb, 1998, Di Carlo et al., 1995, Underwood et al., 1998, Underwood et al., 1997, and Chen et al., 1997). Because vasoconstrictor responses involve more than one endothelin receptor subtype a strategy to inhibit endothelin-1 synthesis may confer greater benefits than trying to find the ideal antagonist to block the effects of endothelin-1 in the pulmonary vasculature. In addition, antagonists of endothelin may have harmful effects by causing hypotension in the peripheral vasculature. Hence, a treatment such as antisense oligonucleotides to preproendothelin-1 administered by inhalation may get over the problems associated with specificity of antagonists, and their adverse effects. Inhalation may restrict their action to the airways and pulmonary vasculature.

Endothelin-1 (ET-1) produces potent vasoconstrictor effects in all vascular beds including the pulmonary circulation. In addition, ET-1 stimulates mitogen-activated protein kinases (MAPK) and can increase smooth muscle mitogenesis (Malarkey et al., 1995). Clinical and experimental studies of PH have shown raised levels of expression and release of ET-1 (Giaid and Saleh, 1995, and Nootens et al., 1995). Administration of the endothelin receptor antagonists reduce both pulmonary vascular resistance and the medial thickening associated with PH induced by chronic hypoxia in rats (Di Carlo et al., 1995, Underwood et al., 1998, Underwood et al., 1997, and Chen et al., 1997). Studies have shown an inverse relationship between the expression of endothelial nitric oxide synthase and the level of ET-1 immunoreactivity in PH, showing that increases in ET-1 are a useful indicator of localized endothelial dysfunction (Giaid and Saleh, 1995).

Despite intense research the factors regulating ET-1 synthesis in vivo have yet to be fully elucidated. However, most evidence suggests an association with endothelial dysfunction and inflammation. Cytokines, including TNFα, stimulate the synthesis and secretion of ET-1 both in vivo and in vitro (Klemm et al., 1995, and Corder et al., 1995). Indeed, TNFα stimulates sufficient ET-1 release to cause vasoconstriction (Klemm et al., 1995). Hence, cytokine stimulated ET-1 synthesis may play a key role in the processes associated with PH, and may be common to both primary PH, and PH occurring in other conditions.

Although obliterative bronchiolitis, asthma, and chronic obstructive pulmonary disease have distinct origins all these conditions display varying degrees of airways remodeling suggesting that there may be a common underlying cause. These conditions are characterized by inflammation with smooth muscle cell proliferation and fibrosis leading to airways obstruction. The precise location of the remodeling may be upper or lower airways depending on the disease. Generally the more advanced the disease the greater the remodeling. Increased endothelin-1 expression has been identified in these conditions, and this may be linked to the remodeling because endothelin-1 stimulates mitogenesis of airways smooth muscle and fibroblasts and induces extracellular matrix production. In addition, endothelin-1 induces bronchoconstriction which may further exacerbate these diseases. Studies characterizing the receptor subtypes mediating these effects have demonstrated roles for endothelin-A, endothelin-B and a putative novel subtype of endothelin receptor. Hence, inhibition of endothelin-1 synthesis using antisense oligonucleotides for preproendothelin-1 may have therapeutic benefits that cannot be obtained using current therapies. In the treatment of obliterative bronchiolitis, asthma, and chronic obstructive pulmonary disease, antisense oligonucleotides to preproendothelin-1 may also be used in combination with other drugs, such as bronchodilators (e.g., beta-adrenergic agonists, methylxanthines, leukotriene antagonists, muscarinic cholinergic antagonists, glucocorticoids$_{13}$ to maximize the benefit and the duration of the period over which these other treatments can be used.

The strategy of using antisense oligonucleotides to preproendothelin-1 for treating primary pulmonary hypertension and these other conditions is a powerful alternative to conventional drug design. It has a number of advantages. The use of aerosolised antisense oligonucleotides will provide a controlled administration to the lungs, thus avoiding the systemic actions that antagonists might have on peripheral cardiovascular function. In addition, by targeting ET-1 synthesis with antisense oligonucleotides, identification of the specific endothelin receptor subtype(s) involved in mediating the pathological processes in these conditions is no longer a concern. Similarly, by providing a treatment which inhibits ET-1 synthesis, the underlying vasoconstrictor response can be abrogated and ET-1 dependent remodeling of the vasculature and airways can be prevented, irrespective of whether the same ET-1 receptor subtypes are involved. In the treatment of PH, antisense oligonucleotides to preproendothelin-1 may also be used in combination with other drugs, such as vasodilators (e.g. prostaglandins, prostaglandin analogues, calcium channel blockers, adenosine or adenosine analogues) to maximize the benefit and the duration of the period over which these other treatments can be used.

In a preferred embodiment, 9-deoxy-2',9-alpha-methano-3-oxa4,5,6-trinor-3,7-(1',3'-interphenylene)-13,14-dihydro-prostaglandin $F_1$, (UT-15) is used as a prostaglandin analogue. The structure of UT-15 is shown below:

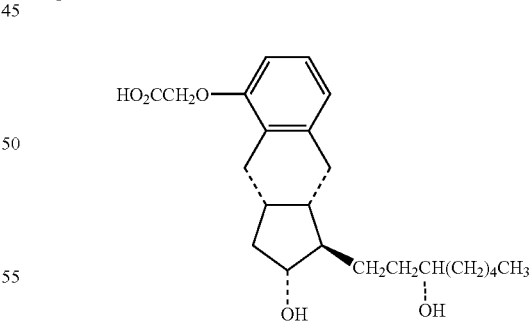

It will be apparent to those skilled in the art that various modifications and variations can be made to the products, compositions and processes of this invention. Thus, it is intended that the present invention cover such modifications and variations, provided they come within the scope of the appended claims and their equivalents.

The disclosure of all publications mentioned above (with citations listed below) are expressly incorporated herein by reference in their entireties to the same extent as if each were incorporated by reference individually. The entire disclosure, including figures, of provisional application Serial No. 60/125,000, filed on Mar. 18, 1999, is hereby incorporated by reference herein.

REFERENCES

Barnes P J (1996) Pathophysiology of asthma. Brit J Clin Pharmacol. 42: 3-10.

Barnes J P (1994) Endothelins and pulmonary disease. J Appl Physiol 77: 1051-9.

Carr M J, Spalding L J, Goldie R G and Henry P J (1998) Distribution of immunoreactive endothelin in the lungs of mice during respiratory viral infection. European Respiratory Journal 11: 79-85.

Chapman K R (1996) Therapeutic approaches to chronic obstructive pulmonary disease: an emerging concensus. Am J. Med. 100 (1A): 5S-10S.

Chen S J, Chen Y F, Opgenorth T J, Wessale J L, Meng Q C, Durand J, DiCarlo V S and Oparil S (1997) The orally active nonpeptide endothelin A-receptor antagonist A-127722 prevents and reverses hypoxia-induced pulmonary hypertension and pulmonary vascular remodeling in Sprague-Dawley rats. J Cardiovasc Pharmacol 29: 713-25.

Corder R, Carrier M, Khan N, Klemm P and Vane J R. (1995) Cytokine regulation of endothelin-1 release from bovine aortic endothelial cells. J. Cardiovasc. Pharmacol. 26 (suppl. 3): S56-S58.

Di Carlo V S, Chen S -J, Meng Q C, Durand J, Yano M, Chen Y -F & Oparil S (1995) ETA-receptor antagonist prevents and reverses chronic hypoxia-induced pulmonary hypertension in rat. Am. J. Physiol. 269: L690-697.

Fukuroda T, Fujikawa T, Ozaki S, Ishikawa K, Yano M and Nishikibe M (1994) Clearance of circulating endothelin-1 by ETB receptors in rats. Biochem. Biophys Res. Commun 199: 1461-1465.

Giaid A and Saleh D (1995) Reduced expression of endothelial nitric oxide synthase in the lungs of patients with pulmonary hypertension. N. Engl; J. Med. 333: 4; 214-221

Hay D W, Luttmann M A, Pullen M A and Nambi P (1998) Functional and binding characterization of endothelin receptors in human bronchus: evidence for a novel endothelin B receptor subtype?. J Pharmacol Exp Ther 284: 669-77

Haynes W G and Webb D J (1998) Endothelin as a regulator of cardiovascular function in health and disease. J. Hypertension 16: 1081-98.

Hoshino M, Nakamura Y and Sim J J (1998) Expression of growth factors and remodelling of the air way wall in bronchial asthma. Thorax. 53: 31-7.

Jeffery P K (1998) Structural and inflammatory changes in COPD: a comparison with asthma. Thorax 53: 129-36.

Jeppsson A, Tazelaar H D, Miller V M and McGregor C G (1998) Distribution of endothelin-1 in transplanted human lungs. Transplantation. 66: 806-9.

Klemm P, Warner T D, Hohlfeld T, Corder R and Vane J R. (1995) Endothelin-1 mediates ex vivo coronary vasoconstriction caused by exogenous and endogenous cytokines. Proc. Natl. Acad. Sci. USA 92: 2691-95

Loffler B M, Breu V and Clozel M (1993) Effect of endothelin receptor antagonists and of the novel non-peptide antagonist Ro 46-2005 on endothelin levels in rat plasma. FEBS Lett 333: 108-110.

Malarkey K, Chilvers E R, Lawson M F and Plevin R (1995) Stimulation by endothelin-1 of mitogen-activated protein kinases and DNA synthesis in bovine tracheal smooth muscle cells. Br. J. Pharmacol. 116: 2267-2273.

Marini M, Carpi S, Bellini A, Patalano F and Mattoli S (1996) Endothelin-1 induces increased fibronectin expression in human bronchial epithelial cells. Biochem Biophys Res Commun 220: 896-9.

Marshall B E and Marshall C (1991) Chap 5.2.6 The Lung: scientific foundations. Eds R G Crystal et al., Raven Press.

McCulloch K M, Docherty C and MacLean M R (1998) Endothelin receptors mediating contraction of rat and human pulmonary resistance arteries: effect of chronic hypoxia in the rat. Brit J Pharmacol 123: 1621-30.

McDermott C D, Shennib H and Giaid A (1998) Immunohistochemical localization of endothelin-1 and endothelin-converting enzyme-1 in rat lung allografts. J Cardiovasc Pharmacol 31 (suppl 1): S27-30.

Nyce J W and Metzer W J (1997) DNA Antisense Therapy for Asthma in an Animal Model. Nature 385: 721-725.

Nootens M, Kaufmann E, Rector T, et al., (1995) Neurohormonal activation in patients with right ventricular failure from pulmonary hypertension: relation to hemodynamic variables and endothelin levels. JAAC 26: 1581-5.

Panettieri R A Jr, Goldie R G, Rigby P J, Eszterhas A J and Hay D W (1996) Endothelin-1-induced potentiation of human airway smooth muscle proliferation: an ETA receptor-mediated phenomenon. Brit J Pharmacol 118: 191-7.

Riley D J (1991) Chap 5.2.7 The Lung: scientific foundations. Eds R G Crystal et al., Raven Press.

Redington A E, Springall D R, Meng Q H, Tuck A B, Holgate S T, Polak J M and Howarth PH (1997) Immunoreactive endothelin in bronchial biopsy specimens: increased expression in asthma and modulation by corticosteroid therapy. Journal of Allergy & Clinical Immunology. 100: 544-52.

Roberts C R (1995) Is ashthma a fibrotic disease? Chest 107 (3) Suppl 111S-117S.

Sun G, Stacey M A, Bellini A, Marini M and Mattoli S (1997) Endothelin-1 induces bronchial myofibroblast differentiation. Peptides 18: 1449-51.

Takeda S, Sawa Y, Minami M, Kaneda Y, Fujii Y, Shirakura R, Yanagisawa M and Matsuda H (1997) Experimental bronchiolitis obliterans induced by in vivo HVJ-liposome-mediated endothelin-1 gene transfer Annals of Thoracic Surgery 63: 1562-7.

Underwood D C, Bochnowicz S, Osborn R R, Louden C S, Hart T K, Ohlstein E H and Hay D W (1998) Chronic hypoxia-induced cardiopulmonary changes in three rat strains: inhibition by the endothelin receptor antagonist SB 217242. J Cardiovasc Pharmacol 31 (Suppl 1): S453-5.

Underwood D C, Bochnowicz S, Osborn R R, Luttmann M A and Hay D W (1997) Nonpeptide endothelin receptor antagonists. X. Inhibition of endothelin-1- and hypoxia-induced pulmonary pressor responses in the guinea pig by the endothelin receptor antagonist, SB 217242. J Pharmac Exp Ther 283: 1130-7.

Wiggs B R, Hrousis C A, Drazen J M and Kamm R D (1997) On the mechanism of mucosal folding in normal and asthmatic airways. J Appl Physiol 83: 1814-21.

SEQUENCE LISTING

<160> NUMBER OF SEQ ID NOS: 61

<210> SEQ ID NO 1
<211> LENGTH: 1166
<212> TYPE: DNA
<213> ORGANISM: Homo sapiens

<400> SEQUENCE: 1

```
ctgcgccagg cgaacgggtc ctgcgcctcc tgcagtccca gctctccacc gccgcgtgcg      60
cctgcagacg ctccgctcgc tgccttctct cctggcaggc gctgcctttt ctccccgtta     120
aagggcactg ggctgaagga tcgctttgag atctgaggaa cccgcagcgc tttgagggac     180
ctgaagctgt ttttcttcgt tttcctttgg gttcagtttg aacggaggt ttttgatccc      240
ttttttcag aatggattat ttgctcatga ttttctctct gctgtttgtg gcttgccaag      300
gagctccaga acagcagtc ttaggcgctg agctcagcgc ggtgggtgag aacgcgggg       360
agaaacccac tcccagtcca ccctggcggc tccgccggtc caagcgctgc tcctgctcgt     420
ccctgatgga taaagagtgt gtctacttct gccacctgga catcatttgg gtcaacactc     480
ccgagcacgt tgttccgtat ggacttggaa gccctaggtc caagagagcc ttggagaatt     540
tacttcccac aaaggcaaca gaccgtgaga atagatgcca atgtgctagc caaaaagaca     600
agaagtgctg gaattttgc caagcaggaa aagaactcag ggctgaagac attatggaga      660
aagactggaa taatcataag aaaggaaaag actgttccaa gcttgggaaa agtgtatt       720
atcagcagtt agtgagagga agaaaaatca gaagaagttc agaggaacac ctaagacaaa     780
ccaggtcgga gaccatgaga aacagcgtca aatcatcttt tcatgatccc aagctgaaag     840
gcaagccctc cagagagcgt tatgtgaccc acaaccgagc acattggtga cagacttcgg     900
ggcctgtctg aagccatagc ctccacggag agccctgtgg ccgactctgc actctccacc     960
ctggctggga tcagagcagg agcatcctct gctggttcct gactggcaaa ggaccagcgt    1020
cctcgttcaa acattccaa gaaaggttaa ggagttcccc caaccatctt cactggcttc     1080
catcagtggt aactgctttg gtctcttctt tcatctgggg atgacaatgg acctctcagc    1140
agaaacacac agtcacattc gaattc                                         1166
```

<210> SEQ ID NO 2
<211> LENGTH: 212
<212> TYPE: PRT
<213> ORGANISM: Homo sapiens

<400> SEQUENCE: 2

```
Met Asp Tyr Leu Leu Met Ile Phe Ser Leu Leu Phe Val Ala Cys Gln
  1               5                  10                  15

Gly Ala Pro Glu Thr Ala Val Leu Gly Ala Glu Leu Ser Ala Val Gly
                 20                  25                  30

Glu Asn Gly Gly Glu Lys Pro Thr Pro Ser Pro Pro Trp Arg Leu Arg
             35                  40                  45

Arg Ser Lys Arg Cys Ser Cys Ser Ser Leu Met Asp Lys Glu Cys Val
         50                  55                  60

Tyr Phe Cys His Leu Asp Ile Ile Trp Val Asn Thr Pro Glu His Val
 65                  70                  75                  80

Val Pro Tyr Gly Leu Gly Ser Pro Arg Ser Lys Arg Ala Leu Glu Asn
                 85                  90                  95
```

```
Leu Leu Pro Thr Lys Ala Thr Asp Arg Glu Asn Arg Cys Gln Cys Ala
        100                 105                 110

Ser Gln Lys Asp Lys Cys Trp Asn Phe Cys Gln Ala Gly Lys Glu
    115                 120                 125

Leu Arg Ala Glu Asp Ile Met Glu Lys Asp Trp Asn Asn His Lys Lys
    130                 135                 140

Gly Lys Asp Cys Ser Lys Leu Gly Lys Lys Cys Ile Tyr Gln Gln Leu
145                 150                 155                 160

Val Arg Gly Arg Lys Ile Arg Arg Ser Ser Glu His Leu Arg Gln
                165                 170                 175

Thr Arg Ser Glu Thr Met Arg Asn Ser Val Lys Ser Ser Phe His Asp
        180                 185                 190

Pro Lys Leu Lys Gly Lys Pro Ser Arg Glu Arg Tyr Val Thr His Asn
        195                 200                 205

Arg Ala His Trp
    210

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 3
cagcccaagt gcccttaac                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 4
ctcaaagcga tccttcagcc                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 5
agctcagcgc ctaagactgc                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 6
tggcagaagt agacacactc                                              20
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 7
ccaaatgatg tccaggtggc                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 8
tggtctccga cctggtttgt                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 9
atgtgctcgg ttgtgggtca                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 10
agcccaagtg ccctttaacg                                              20

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 11
tgatgtccag gtggcagaag ta                                           22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 12
caagtccata cggaacaacg tg                                           22

```
<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 13
catctattct cacggtctgt tg                                                  22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 14
tctcatggtc tccgacctgg tt                                                  22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 15
ggtcacataa cgctctctgg ag                                                  22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 16
gtggagagtg cagagtcggc ca                                                  22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 17
tgatgtccag gtggcagaag                                                     20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 18
gacctggttt gtcttaggtg                                                     20
```

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 19
ggtggagagt gcagagtcgg                                               20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 20
cgcacgcggc ggtggagagc                                               20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 21
aaggcagcga gcggagcgtc                                               20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 22
gcatctattc tcacggtctg                                               20

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 23
catctattct cacggtctg                                                19

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 24
tctattctca cggtctg                                                  17
```

```
<210> SEQ ID NO 25
<211> LENGTH: 86
<212> TYPE: RNA
<213> ORGANISM: Artificial Sequence
<220> FEATURE:
<223> OTHER INFORMATION: Description of Artificial Sequence: Synthetic
      ASON

<400> SEQUENCE: 25
cugcgccagg cgaacggguc cugcgccucc ugcaguccca gcucuccacc gccgcgugcg    60
ccugcagacg cuccgcucgc ugccuu                                        86

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 26
cgagaggtgg cggcgcacgc                                               20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 27
ctgcgaggcg agcgacggaa                                               20

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 28
cgagaggtgg cggcgcac                                                 18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 29
ctgcgaggcg agcgacgg                                                 18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 30
agaggtggcg gcgcacgc                                                 18
```

```
<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 31
gcgaggcgag cgacggaa                                                   18

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 32
cgagaggtgg cggcgc                                                     16

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 33
ctgcgaggcg agcgac                                                     16

<210> SEQ ID NO 34
<211> LENGTH: 16
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 34
aggtggcggc gcacgc                                                     16

<210> SEQ ID NO 35
<211> LENGTH: 16
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 35
gaggcgagcg acggaa                                                     16

<210> SEQ ID NO 36
<211> LENGTH: 16
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 36
agaggtggcg gcgcac                                                     16
```

<210> SEQ ID NO 37
<211> LENGTH: 16
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 37
gcgaggcgag cgacgg                                                      16

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 38
gacgcggtcc gcttgcccag                                                  20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 39
gcttgcccag gacgcggagg                                                  20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 40
gacgcggagg acgtcagggt                                                  20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 41
ggaggacgtc agggtcgaga                                                  20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 42
gtggcggcgc acgcggacgt                                                  20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 43
ggacgtctgc gaggcgagcg                                                   20

<210> SEQ ID NO 44
<211> LENGTH: 104
<212> TYPE: RNA
<213> ORGANISM: Artificial Sequence
<220> FEATURE:
<223> OTHER INFORMATION: Description of Artificial Sequence: Synthetic
      ASON

<400> SEQUENCE: 44
cucuccuggc aggcgcugcc uuuucucccc guuaaagggc acuugggcug aaggaucgcu      60
uugagaucug aggaacccgc agcgcuuuga gggaccugaa gcug                       104

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 45
caatttcccg tgaacccgac                                                   20

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 46
caatttcccg tgaacccg                                                     18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 47
atttcccgtg aacccgac                                                     18

<210> SEQ ID NO 48
<211> LENGTH: 16
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 48
caatttcccg tgaacc                                                       16

```
<210> SEQ ID NO 49
<211> LENGTH: 16
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 49
ttcccgtgaa cccgac                                                         16

<210> SEQ ID NO 50
<211> LENGTH: 16
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 50
atttcccgtg aacccg                                                         16

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 51
gcaatttccc gtgaacccga                                                     20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 52
gagaggaccg tccgcgacgg                                                     20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 53
ccgacttcct agcgaaactc                                                     20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 54
gggcaatttc ccgtgaaccc                                                     20
```

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic ASON

<400> SEQUENCE: 55
gaaactctag actccttggg                                              20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic ASON

<400> SEQUENCE: 56
tgggcgtcgc gaaactccct                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic ASON

<400> SEQUENCE: 57
gaaactccct ggacttcgac                                              20

<210> SEQ ID NO 58
<211> LENGTH: 80
<212> TYPE: RNA
<213> ORGANISM: Artificial Sequence
<220> FEATURE:
<223> OTHER INFORMATION: Description of Artificial Sequence: Synthetic ASON

<400> SEQUENCE: 58
uuuuucuucg uuuuccuuug gguucaguuu gaacgggagg uuuuugaucc cuuuuuuca   60 gaauggauua uuugcucaug                                              80

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic ASON

<400> SEQUENCE: 59
cccaagtcaa acttgccctc                                              20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic ASON

<400> SEQUENCE: 60
gtcttaccta ataaacgagt                                              20

```
<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      ASON

<400> SEQUENCE: 61
cttacctaat aaacgagtac                                              20
```

What is claimed is:

1. An isolated antisense oligonucleotide complementary to human preproendothelin-1 mRNA, the isolated antisense oligonucleotide having no more than 32 nucleotide base pairs, wherein the antisense oligonucleotide comprises an oligonucleotide consisting of nucleotide sequence WH11 (SEQ ID No:21) or WH11A (SEQ ID No:29).

2. An antisense oligonucleotide composition, comprising the isolated antisense oligonucleotide of claim 1 and a transfectant.

3. The composition of claim 2, formulated as an aerosol or powder.

4. An antisense oligonucleotide composition, comprising the isolated antisense oligonucleotide of claim 1 and at least one drug that inhibits vasoconstriction.

5. The composition of claim 4, wherein the vasoconstriction drug is a prostaglandin, prostaglandin analog, calcium channel blocker, adenosine or adenosine analog.

6. The composition of claim 4, wherein the drug is 9-deoxy-2', 9-alpha-methano-3-oxa-4,5,6-trinor-3,7-(1',3'-interphenylene)-1-3,14-dihydro-prostaglandin $F_1$, or a prodrug analog thereof.

* * * * *